(12) United States Patent
Sun et al.

(10) Patent No.: US 12,186,591 B2
(45) Date of Patent: Jan. 7, 2025

(54) X-RAY IMAGING SYSTEM FOR RADIATION THERAPY

(71) Applicant: SHANGHAI UNITED IMAGING HEALTHCARE CO., LTD., Shanghai (CN)

(72) Inventors: Buliang Sun, Shanghai (CN); Cheng Ni, Shanghai (CN); Wei Zhang, Shanghai (CN); Li Wang, Shanghai (CN); Tao Liu, Shanghai (CN); Jianwei Fu, Shanghai (CN); Libo Fang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/180,811

(22) Filed: Mar. 8, 2023

(65) Prior Publication Data

US 2023/0241416 A1    Aug. 3, 2023

Related U.S. Application Data

(63) Continuation of application No. PCT/CN2021/080639, filed on Mar. 12, 2021, which
(Continued)

(30) Foreign Application Priority Data

Nov. 7, 2020  (CN) .......................... 202011234813.9
Nov. 13, 2020 (CN) .......................... 202011271345.2
Dec. 14, 2020 (CN) .......................... 202011468108.5

(51) Int. Cl.
*A61N 5/10* (2006.01)
*A61B 6/03* (2006.01)
(Continued)

(52) U.S. Cl.
CPC ............ *A61N 5/1069* (2013.01); *A61B 6/035* (2013.01); *A61B 6/4007* (2013.01);
(Continued)

(58) Field of Classification Search
None
See application file for complete search history.

(56) References Cited

U.S. PATENT DOCUMENTS 6,661,870 B2    12/2003  Kapatoes et al.
2003/0048868 A1 *  3/2003  Bailey .................... A61B 6/032
                                                                378/65
(Continued)

FOREIGN PATENT DOCUMENTS

CN       107184225 A      9/2017
CN       207765764 U      8/2018
(Continued)

OTHER PUBLICATIONS

International Search Report in PCT/CN2021/138130 mailed on Mar. 11, 2022, 5 pages.
(Continued)

*Primary Examiner* — Hoon K Song
(74) *Attorney, Agent, or Firm* — METIS IP LLC

(57) ABSTRACT

The present disclosure may provide a radiation system. The radiation system may include a treatment head, a detector, a plurality of imaging sources, and a gantry. The treatment head, the detector, and the plurality of imaging sources may be mounted on the gantry. The treatment head may be configured to deliver a treatment beam toward an object. The plurality of imaging sources may be configured to deliver a plurality of imaging beams toward the object. At least two of the plurality of imaging sources may share the detector. The detector may be configured to detect at least two of the plurality of imaging beams. The detected at least two
(Continued)

imaging beams may be emitted by different imaging sources of the at least two imaging sources.

17 Claims, 13 Drawing Sheets

Related U.S. Application Data is a continuation-in-part of application No. 17/015,033, filed on Sep. 8, 2020, now Pat. No. 11,883,687.

(51) Int. Cl.
    *A61B 6/40*     (2024.01)
    *A61B 6/42*     (2024.01)

(52) U.S. Cl.
    CPC .......... *A61B 6/4291* (2013.01); *A61N 5/1045* (2013.01); *A61N 5/1049* (2013.01); *A61N 5/1071* (2013.01); *A61N 5/1081* (2013.01); *A61N 2005/1061* (2013.01)

(56) References Cited

U.S. PATENT DOCUMENTS

| | | |
|---|---|---|
| 2006/0074304 A1 | 4/2006 | Sayeh |
| 2007/0003007 A1 | 1/2007 | Carrano et al. |
| 2007/0003021 A1 | 1/2007 | Guertin et al. |
| 2007/0003123 A1 | 1/2007 | Fu et al. |
| 2007/0016014 A1 | 1/2007 | Hara et al. |
| 2007/0211856 A1* | 9/2007 | Urano ................. A61N 5/1049 378/65 |
| 2008/0002809 A1 | 1/2008 | Bodduluri |
| 2008/0205588 A1 | 8/2008 | Kim |
| 2010/0290586 A1* | 11/2010 | Friedrich ............. A61B 6/4014 378/65 |
| 2011/0040170 A1 | 2/2011 | Geva et al. |
| 2011/0182410 A1 | 7/2011 | Balakin |
| 2012/0035470 A1 | 2/2012 | Kuduvalli et al. |
| 2012/0129360 A1 | 5/2012 | Angerpointner et al. |
| 2012/0230465 A1 | 9/2012 | Matsuzawa et al. |
| 2013/0256551 A1 | 10/2013 | Yao |
| 2013/0266202 A1 | 10/2013 | Yamada et al. |
| 2014/0247919 A1 | 9/2014 | Zhang et al. |
| 2015/0182175 A1 | 7/2015 | Handa et al. |
| 2016/0262709 A1* | 9/2016 | Siewerdsen .......... A61B 6/4035 |
| 2016/0303401 A1 | 10/2016 | Mostafavi et al. |
| 2017/0106208 A1 | 4/2017 | Gauthier et al. |
| 2018/0192978 A1 | 7/2018 | Naylor et al. |
| 2018/0304098 A1 | 10/2018 | Humber et al. |
| 2019/0000406 A1 | 1/2019 | Liu et al. |
| 2019/0168025 A1 | 6/2019 | Koponen et al. |
| 2019/0175945 A1 | 6/2019 | Yan et al. |
| 2019/0209868 A1 | 7/2019 | Stahl et al. |
| 2019/0209869 A1 | 7/2019 | Liu et al. |
| 2019/0336793 A1 | 11/2019 | Zhou et al. |
| 2019/0336795 A1 | 11/2019 | Zhou et al. |
| 2019/0380666 A1 | 12/2019 | Sheng et al. |
| 2020/0170591 A1* | 6/2020 | Gagnon ................. A61B 6/027 |
| 2020/0406064 A1 | 12/2020 | Maltz et al. |
| 2021/0030380 A1* | 2/2021 | Subrahmanyam ... A61B 6/4014 |
| 2021/0267683 A1 | 9/2021 | Brown |

FOREIGN PATENT DOCUMENTS

| | | |
|---|---|---|
| CN | 108514694 A | 9/2018 |
| CN | 109224320 A | 1/2019 |
| CN | 214013363 U | 8/2021 |
| CN | 215605797 U | 1/2022 |
| EP | 3056245 A1 | 8/2016 |
| WO | 2012055098 A1 | 5/2012 |
| WO | 2012099747 A2 | 7/2012 |
| WO | 2018093933 A1 | 5/2018 |
| WO | 2018176016 A1 | 9/2018 |

OTHER PUBLICATIONS

Written Opinion in PCT/CN2021/138130 mailed on Mar. 11, 2022, 5 pages.
International Search Report in PCT/CN2021/110163 mailed on Sep. 28, 2021, 5 pages.
Written Opinion in PCT/CN2021/110163 mailed on Sep. 28, 2021, 6 pages.
International Search Report in PCT/CN2021/080639 mailed on Aug. 19, 2021, 5 pages.
Written Opinion in PCT/CN2021/080639 mailed on Aug. 19, 2021, 5 pages.

\* cited by examiner

1200

| Causing the plurality of imaging sources of the radiation system to emit a plurality of imaging beams of different energy levels toward an object and the detector | — 1210 |

| Generating an image of the object based on at least a part of the plurality of imaging beams of different energy levels detected by the detector | — 1220 |

FIG. 12

X-RAY IMAGING SYSTEM FOR RADIATION THERAPY

CROSS-REFERENCE TO THE RELATED APPLICATIONS

This application is a continuation of International Patent Application No. PCT/CN2021/080639, filed on Mar. 12, 2021, which claims priority of U.S. patent application Ser. No. 17/015,033 filed on Sep. 8, 2020, Chinese Application No. 202011234813.9 filed on Nov. 7, 2020, Chinese Application No. CN202011271345.2 filed on Nov. 13, 2020, and Chinese Application No. CN202011468108.5 filed on Dec. 14, 2020, the contents of each of which are hereby incorporated by reference.

TECHNICAL FIELD

The present disclosure generally relates to medical technology, and more particularly, systems and methods for imaging systems for radiation therapy.

BACKGROUND

Radiation therapy is a localized treatment for a specific target tissue (a target volume), such as a cancerous tumor. Dosimetric and geometric data are checked before, after, or during the treatment, to ensure correct patient placement and that the administered radiotherapy treatment matches the previously planned treatment. This process is referred to as image-guided radiation therapy (IGRT), and involves the use of an imaging system to view target tissues while radiation treatment is delivered to the target volume.

SUMMARY

According to one aspect of the present disclosure, a radiation system may be provided. The radiation system may include: a gantry; a treatment head configured to deliver a treatment beam toward an object; a detector; and a plurality of imaging sources configured to deliver a plurality of imaging beams toward the object. The treatment head, the detector, and the plurality of imaging sources may be mounted on the gantry. At least two of the plurality of imaging sources may share the detector. The detector may be configured to detect at least two of the plurality of imaging beams. The detected at least two imaging beams may be emitted by different imaging sources of the at least two imaging sources.

In some embodiments, the treatment head, the detector, and the plurality of imaging sources may be located in a same plane.

In some embodiments, the plane may be perpendicular to a gantry axis of the gantry.

In some embodiments, the plurality of imaging sources may include a computed tomography (CT) imaging source and at least one digital radiography (DR) imaging source.

In some embodiments, the plurality of imaging sources may include two DR imaging sources.

In some embodiments, an angle between axes of two imaging beams emitted by the two DR imaging sources may be smaller than or equal to 90 degrees.

In some embodiments, an angle between an axis of an imaging beam emitted by the CT imaging source and an axis of a treatment beam emitted by the treatment head may be 90 degrees.

In some embodiments, an axis of an imaging beam emitted by the CT imaging source may be perpendicular to the detector at a center of the detector.

In some embodiments, the at least one DR imaging source may include at least two DR imaging sources. The CT imaging source may be located between two of the at least two DR imaging sources.

In some embodiments, the radiation system may include a collimator configured to adjust a fan angle of an imaging beam emitted by the CT imaging source.

In some embodiments, the detector may include an anti-scatter grid.

In some embodiments, the anti-scatter grid may include a plurality of portions. An orientation of each of the plurality of portions may be adjustable relative to at least one of the at least one DR imaging source.

In some embodiments, the orientation of at least one of the plurality of portions of the anti-scatter grid may be adjustable to correspond to a direction of at least one imaging beam emitted by the at least one DR imaging source.

In some embodiments, a detection range of the detector may encompass an aggregate field of view of the plurality of imaging sources.

In some embodiments, at least two of the plurality of imaging beams may be of different energy levels.

In some embodiments, at least one of the plurality of imaging sources may be configured to emit imaging beams of different energy levels.

In some embodiments, a width of the detector may exceed a threshold.

In some embodiments, the detector may include a curvilinear detector.

In some embodiments, the gantry may include a rotatable roller. The treatment head, the detector, and the plurality of imaging sources may be mounted on the rotatable roller and rotate with the rotatable roller.

According to another aspect of the present disclosure. A system may be provided. The system may include at least one storage device including a set of instructions and at least one processor in communication with the at least one storage device and a radiation system. The radiation system may include a plurality of imaging sources and a detector. At least two of the plurality of imaging sources may share the detector. The detector may be configured to detect at least two imaging beams emitted by the at least two imaging sources. The detected at least two imaging beams may be emitted by different imaging sources of the at least two imaging sources. When executing the set of instructions, the at least one processor may be configured to cause the system to perform operations including: generating a pre-treatment image by causing the CT imaging source of the radiation system to emit a pre-treatment imaging beam toward an object; determining position information of a target region of the object in the radiation system based on the pre-treatment image; and causing the target region of the object to be positioned in the radiation system according to the position information.

In some embodiments, the at least one processor may be configured to cause the system to perform the operations including: generating a second pre-treatment image by causing at least one of the plurality of imaging sources to emit at least one second pre-treatment imaging beam toward the object, wherein the second pre-treatment image is a multi-energy image; and adjusting a treatment plan of the target region of the object based on the pre-treatment image and the second pre-treatment image.

In some embodiments, the adjusting a treatment plan of the target region of the object based on the pre-treatment image and the second pre-treatment image may include: generating a fused image by fusing the pre-treatment image and the second pre-treatment image; determine information of the target region in the fused image; and adjusting the treatment plan of the target region of the object based on the information of the target region.

In some embodiments, the at least one second pre-treatment imaging beam may include at least two second pre-treatment imaging beams that are of different energy levels and emitted by at least two of the plurality of imaging sources.

In some embodiments, the at least one of the plurality of imaging sources may include one of the plurality of imaging sources that is configured to emit imaging beams of different energy levels.

In some embodiments, one of the at least one second pre-treatment imaging beam that is emitted by the CT imaging source may be adjustably collimated by a collimator of the radiation system.

In some embodiments, a first fan angle of the second pre-treatment imaging beam may be smaller than or equal to a second fan angle of the pre-treatment imaging beam.

In some embodiments, the at least one processor may be configured to cause the system to perform the operations including: causing a treatment head of the radiation system to deliver a treatment beam toward the target region of the object based on a treatment plan of the object and the position information of the target region; generating a plurality of images of the object by causing the plurality of imaging sources of the radiation system to deliver a plurality of treatment imaging beams toward the object; and adjusting a delivery of the treatment beam or adjusting the position information of the target region based on the plurality of images of the object.

In some embodiments, the adjusting a delivery of the treatment beam may include at least one of adjusting a direction of the treatment beam to allow the treatment beam toward the target region; adjusting the treatment plan, or pausing emission of the treatment beam.

In some embodiments, one of the plurality of treatment imaging beams that is emitted by the CT imaging source may be adjustably collimated by a collimator of the radiation system.

In some embodiments, a first fan angle of one of the plurality of treatment imaging beams that is emitted by the CT imaging source may be smaller than or equal to a second fan angle of the pre-treatment imaging beam.

In some embodiments, the image may include at least one organ of the object. The adjusting a delivery of the treatment beam or adjusting the position information of the target region may include: determining motion information of the at least one organ based on the image; and adjusting the delivery of the treatment beam or adjusting the position information of the target region based on the motion information of the at least one organ.

In some embodiments, the motion information of the at least one organ may relate to a motion of the at least one organ.

According to another aspect of the present disclosure, a system may be provided. The system may include at least one storage device including a set of instructions and at least one processor in communication with the at least one storage device and a radiation system. The radiation system may include a first detector and a plurality of imaging sources one of which is a CT imaging source. At least two of the plurality of imaging sources may share the first detector. The first detector may be configured to detect at least two imaging beams emitted by the at least two imaging sources. The detected at least two imaging beams may be emitted by different imaging sources of the at least two imaging sources. When executing the set of instructions, the at least one processor may be configured to cause the system to perform operations including: generating a pre-treatment image by causing the CT imaging source of the radiation system to emit a pre-treatment imaging beam toward an object; causing a target region of the object to be positioned in the radiation system based on the pre-treatment image; causing a treatment head of the radiation system to deliver, based on a treatment plan of the object, at least one treatment beam toward the target region of the object; generating at least one treatment image based on at least a portion of the at least one treatment beam detected by a second detector of the radiation system; and determining, based on the pre-treatment image and the at least one treatment image, whether a delivery of the treatment beam conforms to a planned treatment beam delivery according to the treatment plan.

In some embodiments, the at least one treatment image may include one treatment image. The determining, based on the pre-treatment image and the at least one treatment image, whether a delivery of the treatment beam conforms to a planned treatment beam delivery according to the treatment plan may include: determining a reference treatment image based on the pre-treatment image and the treatment plan of the object; generating a comparison result by comparing the reference treatment image and the treatment image; and determining whether the delivery of the treatment beam conforms to the planned treatment beam delivery of the treatment plan based on the comparison result.

In some embodiments, the treatment image and the reference treatment image may be both two-dimensional and from a same view of the object.

In some embodiments, the at least one treatment image may include a plurality of treatment images from at least two different views of the object. The determining, based on the pre-treatment image and the at least one treatment image, whether a delivery of the treatment beam conforms to a planned treatment beam delivery according to the treatment plan may include: estimating a radiation dose distribution of the treatment beam in the object based on the pre-treatment image and the plurality of treatment images; generating a comparison result by comparing the radiation dose distribution of the treatment beam and a planned radiation dose distribution in the object; and determining whether the delivery of the treatment beam conforms to the planned treatment beam delivery of the treatment plan based on the comparison result.

In some embodiments, the radiation dose distribution of the treatment beam in the object may include a three-dimensional radiation dose distribution.

According to another aspect of the present disclosure, a system may be provided. The system may include at least one storage device including a set of instructions and at least one processor in communication with the at least one storage device and a radiation system. The radiation system may include a detector and a plurality of imaging sources one of which is a CT imaging source. When executing the set of instructions, the at least one processor may be configured to cause the system to perform operations including: causing a treatment head of the radiation system to deliver a treatment beam toward a target region of an object based on a treatment plan of the object; causing the plurality of imaging sources of the radiation system to emit a plurality of imaging beams toward the object and the detector, wherein the plurality of imaging beams include a CT imaging beam emitted by the CT imaging source, and the CT imaging beam is of a fan angle achieved by adjusting an aperture of a collimator of the CT imaging source; generating a group of images of the object based on at least a part of the plurality of imaging beams detected by the detector; and determining position information of the target region based on the group of images of the object.

In some embodiments, each of the plurality of imaging beams may impinge on a detection region of the detector. The plurality of detection regions may be at least partially separated from each other.

In some embodiments, at least one of the plurality of imaging sources may rotate with the treatment head.

In some embodiments, at least one of the plurality of imaging beams and the treatment beam may be emitted concurrently.

In some embodiments, at least two of the plurality of images may be from different views of the object.

In some embodiments, at least one image of the group of images may be two-dimensional.

In some embodiments, the plurality of images may include organ information of at least one organ of the object, a motion of the target region relating to a motion of the at least one organ. The determining position information of the target region based on the plurality of images of the object may include: determining motion information of the at least one organ based on the organ information; and determining the position information of the target region based on the motion information of the at least one organ.

In some embodiments, the at least one processor may be configured to cause the system to perform the operations including: generating a second group of images of the object by causing the plurality of imaging sources to deliver a second plurality of imaging beams toward the object and the detector, the second plurality of imaging beams including a second CT imaging beam of the fan angle emitted by the CT imaging source; and determining second position information of the target region based on the second group of images of the object.

In some embodiments, the group of images of the object may correspond to a first time point. The second group of images of the object may correspond to a second time point that is different from the first time point.

According to another aspect of the present disclosure, a system may be provided. The system may include at least one storage device including a set of instructions and at least one processor in communication with the at least one storage device and a radiation system. The radiation system may include a detector and a plurality of imaging sources one of which is a CT imaging source. When executing the set of instructions, the at least one processor may be configured to cause the system to perform operations including: causing the plurality of imaging sources of the radiation system to emit a plurality of imaging beams of different energy levels toward an object and the detector, wherein the plurality of imaging beams include a CT imaging beam emitted by the CT imaging source, and the CT imaging beam is of a fan angle achieved by adjusting an aperture of a collimator of the CT imaging source; and generating an image of the object based on at least a part of the plurality of imaging beams of different energy levels detected by the detector.

In some embodiments, the image of the object may be a multi-energy image.

In some embodiments, the at least one processor may be configured to cause the system to perform the operations including: causing the CT imaging source to emit a second CT imaging beam of a second fan angle achieved by adjusting the aperture of the collimator of the CT imaging source, the second fan angle being larger than the fan angle; generating a second image based on at least a part of the second CT imaging beam detected by the detector; generating a fused image by fusing the image and the second image; and determining information of a target region in the fused image.

In some embodiments, the information of the target region in the fused image may include at least one of a contour of the target region or a contour of a tissue surrounding the target region.

In some embodiments, the at least one processor may be configured to cause the system to perform the operations including: adjusting, based on the information of the target region in the fused image, a treatment plan regarding the target region of the object.

According to another aspect of the present disclosure, a method may be provided. The method may be implemented on a radiation system and a computing device having at least one processor, and at least one storage device. The radiation system may include a plurality of imaging sources and a detector. At least two of the plurality of imaging sources may share the detector. The detector may be configured to detect at least two imaging beams emitted by the at least two imaging sources. The detected at least two imaging beams may be emitted by different imaging sources of the at least two imaging sources. The method may include: generating a pre-treatment image by causing the CT imaging source of the radiation system to emit a pre-treatment imaging beam toward an object; determining position information of a target region of the object in the radiation system based on the pre-treatment image; and causing the target region of the object to be positioned in the radiation system according to the position information.

In some embodiments, the method may include: generating a second pre-treatment image by causing at least one of the plurality of imaging sources to emit at least one second pre-treatment imaging beam toward the object, wherein the second pre-treatment image is a multi-energy image; and adjusting a treatment plan of the target region of the object based on the pre-treatment image and the second pre-treatment image.

In some embodiments, the adjusting a treatment plan of the target region of the object based on the pre-treatment image and the second pre-treatment image may include: generating a fused image by fusing the pre-treatment image and the second pre-treatment image; determine information of the target region in the fused image; and adjusting the treatment plan of the target region of the object based on the information of the target region.

In some embodiments, the at least one second pre-treatment imaging beam may include at least two second pre-treatment imaging beams that are of different energy levels and emitted by at least two of the plurality of imaging sources.

In some embodiments, the at least one of the plurality of imaging sources may include one of the plurality of imaging sources that is configured to emit imaging beams of different energy levels.

In some embodiments, one of the at least one second pre-treatment imaging beam that is emitted by the CT imaging source may be adjustably collimated by a collimator of the radiation system.

In some embodiments, a first fan angle of the second pre-treatment imaging beam may be smaller than or equal to a second fan angle of the pre-treatment imaging beam.

In some embodiments, the method may include causing a treatment head of the radiation system to deliver a treatment beam toward the target region of the object based on a treatment plan of the object and the position information of the target region; generating a plurality of images of the object by causing the plurality of imaging sources of the radiation system to deliver a plurality of treatment imaging beams toward the object; and adjusting a delivery of the treatment beam or adjusting the position information of the target region based on the plurality of images of the object.

In some embodiments, the adjusting a delivery of the treatment beam may include at least one of adjusting a direction of the treatment beam to allow the treatment beam toward the target region; adjusting the treatment plan, or pausing emission of the treatment beam.

In some embodiments, one of the plurality of treatment imaging beams that is emitted by the CT imaging source may be adjustably collimated by a collimator of the radiation system.

In some embodiments, a first fan angle of one of the plurality of treatment imaging beams that is emitted by the CT imaging source may be smaller than or equal to a second fan angle of the pre-treatment imaging beam.

In some embodiments, the image may include at least one organ of the object. The adjusting a delivery of the treatment beam or adjusting the position information of the target region may include: determining motion information of the at least one organ based on the image; and adjusting the delivery of the treatment beam or adjusting the position information of the target region based on the motion information of the at least one organ.

In some embodiments, the motion information of the at least one organ may relate to a motion of the at least one organ.

According to another aspect of the present disclosure, a method may be provided. The method may be implemented on a radiation system and a computing device having at least one processor, and at least one storage device. The radiation system may include a first detector and a plurality of imaging sources one of which is a CT imaging source. At least two of the plurality of imaging sources may share the first detector. The first detector may be configured to detect at least two imaging beams emitted by the at least two imaging sources. The detected at least two imaging beams may be emitted by different imaging sources of the at least two imaging sources. The method may include: generating a pre-treatment image by causing the CT imaging source of the radiation system to emit a pre-treatment imaging beam toward an object; causing a target region of the object to be positioned in the radiation system based on the pre-treatment image; causing a treatment head of the radiation system to deliver, based on a treatment plan of the object, at least one treatment beam toward the target region of the object; generating at least one treatment image based on at least a portion of the at least one treatment beam detected by a second detector of the radiation system; and determining, based on the pre-treatment image and the at least one treatment image, whether a delivery of the treatment beam conforms to a planned treatment beam delivery according to the treatment plan.

In some embodiments, the at least one treatment image may include one treatment image. The determining, based on the pre-treatment image and the at least one treatment image, whether a delivery of the treatment beam conforms to a planned treatment beam delivery according to the treatment plan may include: determining a reference treatment image based on the pre-treatment image and the treatment plan of the object; generating a comparison result by comparing the reference treatment image and the treatment image; and determining whether the delivery of the treatment beam conforms to the planned treatment beam delivery of the treatment plan based on the comparison result.

In some embodiments, the treatment image and the reference treatment image may be both two-dimensional and from a same view of the object.

In some embodiments, the at least one treatment image may include a plurality of treatment images from at least two different views of the object. The determining, based on the pre-treatment image and the at least one treatment image, whether a delivery of the treatment beam conforms to a planned treatment beam delivery according to the treatment plan may include: estimating a radiation dose distribution of the treatment beam in the object based on the pre-treatment image and the plurality of treatment images; generating a comparison result by comparing the radiation dose distribution of the treatment beam and a planned radiation dose distribution in the object; and determining whether the delivery of the treatment beam conforms to the planned treatment beam delivery of the treatment plan based on the comparison result.

In some embodiments, the radiation dose distribution of the treatment beam in the object may include a three-dimensional radiation dose distribution.

According to another aspect of the present disclosure, a method may be provided. The method may be implemented on a radiation system and a computing device having at least one processor, and at least one storage device. The radiation system may include a detector and a plurality of imaging sources one of which is a CT imaging source. The method may include: causing a treatment head of the radiation system to deliver a treatment beam toward a target region of an object based on a treatment plan of the object; causing the plurality of imaging sources of the radiation system to emit a plurality of imaging beams toward the object and the detector, wherein the plurality of imaging beams include a CT imaging beam emitted by the CT imaging source, and the CT imaging beam is of a fan angle achieved by adjusting an aperture of a collimator of the CT imaging source; generating a group of images of the object based on at least a part of the plurality of imaging beams detected by the detector; and determining position information of the target region based on the group of images of the object.

In some embodiments, each of the plurality of imaging beams may impinge on a detection region of the detector. The plurality of detection regions may be at least partially separated from each other.

In some embodiments, at least one of the plurality of imaging sources may rotate with the treatment head.

In some embodiments, at least one of the plurality of imaging beams and the treatment beam may be emitted concurrently.

In some embodiments, at least two of the plurality of images may be from different views of the object.

In some embodiments, at least one image of the group of images may be two-dimensional.

In some embodiments, the plurality of images may include at least one organ of the object. A motion of the target region may relate to a motion of the at least one organ. The determining position information of the target region based on the plurality of images of the object may include:

determining motion information of the at least one organ based on the plurality of images; and determining the position information of the target region based on the motion information of the at least one organ.

In some embodiments, the method may include: generating a second group of images of the object by causing the plurality of imaging sources to deliver a second plurality of imaging beams toward the object and the detector, the second plurality of imaging beams including a second CT imaging beam of the fan angle emitted by the CT imaging source; and determining second position information of the target region based on the second group of images of the object.

In some embodiments, the group of images of the object may correspond to a first time point. The second group of images of the object may correspond to a second time point that is different from the first time point.

According to another aspect of the present disclosure, a method may be provided. The method may be implemented on a radiation system and a computing device having at least one processor, and at least one storage device. The radiation system may include a detector and a plurality of imaging sources one of which is a CT imaging source. The method may include: causing the plurality of imaging sources of the radiation system to emit a plurality of imaging beams of different energy levels toward an object and the detector, wherein the plurality of imaging beams include a CT imaging beam emitted by the CT imaging source, and the CT imaging beam is of a fan angle achieved by adjusting an aperture of a collimator of the CT imaging source; and generating an image of the object based on at least a part of the plurality of imaging beams of different energy levels detected by the detector.

In some embodiments, the image of the object may be a multi-energy image.

In some embodiments, the method may include: causing the CT imaging source to emit a second CT imaging beam of a second fan angle achieved by adjusting the aperture of the collimator of the CT imaging source, the second fan angle being larger than the fan angle; generating a second image based on at least a part of the second CT imaging beam detected by the detector; generating a fused image by fusing the image and the second image; and determining information of a target region in the fused image.

In some embodiments, the information of the target region in the fused image may include at least one of a contour of the target region or a contour of a tissue surrounding the target region.

In some embodiments, the method may include: adjusting, based on the information of the target region in the fused image, a treatment plan regarding the target region of the object.

According to another aspect of the present disclosure, a non-transitory computer readable medium may be provided. The non-transitory computer readable medium may include instructions being executed by at least one processor, causing the at least one processor to implement a method on a radiation system. The radiation system may include a plurality of imaging sources and a detector. At least two of the plurality of imaging sources may share the detector. The detector may be configured to detect at least two imaging beams emitted by the at least two imaging sources. The detected at least two imaging beams may be emitted by different imaging sources of the at least two imaging sources. The method may include: generating a pre-treatment image by causing the CT imaging source of the radiation system to emit a pre-treatment imaging beam toward an object; determining position information of a target region of the object in the radiation system based on the pre-treatment image; and causing the target region of the object to be positioned in the radiation system according to the position information.

According to another aspect of the present disclosure, a non-transitory computer readable medium may be provided. The non-transitory computer readable medium may include: instructions being executed by at least one processor, causing the at least one processor to implement a method on a radiation system. The radiation system may include a first detector and a plurality of imaging sources one of which is a CT imaging source. At least two of the plurality of imaging sources may share the first detector. The first detector may be configured to detect at least two imaging beams emitted by the at least two imaging sources. The detected at least two imaging beams may be emitted by different imaging sources of the at least two imaging sources. The method may include: generating a pre-treatment image by causing the CT imaging source of the radiation system to emit a pre-treatment imaging beam toward an object; causing a target region of the object to be positioned in the radiation system based on the pre-treatment image; causing a treatment head of the radiation system to deliver, based on a treatment plan of the object, at least one treatment beam toward the target region of the object; generating at least one treatment image based on at least a portion of the at least one treatment beam detected by a second detector of the radiation system; and determining, based on the pre-treatment image and the at least one treatment image, whether a delivery of the treatment beam conforms to a planned treatment beam delivery according to the treatment plan.

According to another aspect of the present disclosure, a non-transitory computer readable medium may be provided. The non-transitory computer readable medium may include instructions being executed by at least one processor, causing the at least one processor to implement a method on a radiation system. The radiation system may include a detector and a plurality of imaging sources one of which is a CT imaging source. The method may include: causing a treatment head of the radiation system to deliver a treatment beam toward a target region of an object based on a treatment plan of the object; causing the plurality of imaging sources of the radiation system to emit a plurality of imaging beams toward the object and the detector, wherein the plurality of imaging beams include a CT imaging beam emitted by the CT imaging source, and the CT imaging beam is of a fan angle achieved by adjusting an aperture of a collimator of the CT imaging source; generating a group of images of the object based on at least a part of the plurality of imaging beams detected by the detector; and determining position information of the target region based on the group of images of the object.

According to another aspect of the present disclosure, a non-transitory computer readable medium may be provided. The non-transitory computer readable medium may include: instructions being executed by at least one processor, causing the at least one processor to implement a method on a radiation system. The radiation system may include a detector and a plurality of imaging sources one of which is a CT imaging source. The method may include: causing the plurality of imaging sources of the radiation system to emit a plurality of imaging beams of different energy levels toward an object and the detector, wherein the plurality of imaging beams include a CT imaging beam emitted by the CT imaging source, and the CT imaging beam is of a fan angle achieved by adjusting an aperture of a collimator of the CT imaging source; and generating an image of the object based on at least a part of the plurality of imaging beams of different energy levels detected by the detector.

According to another aspect of the present disclosure, a radiation system may be provided. The system may include: a gantry; a treatment head configured to deliver a treatment beam toward an object; a plurality of imaging sources configured to deliver a plurality of imaging beams toward the object, the plurality of imaging sources comprising a first imaging source of a first type and a second imaging source of a second type that is different from the first type, and the first imaging source of the first type being a CT imaging source; and at least one detector configured to detect a plurality of imaging beams emitted by the plurality of imaging sources. The at least one detector and the plurality of imaging sources may be mounted on the gantry. The plurality of imaging beams and the treatment beam may traverse a same plane of the object.

In some embodiments, the at least one detector may include one detector. The first imaging source and the second imaging source may share the detector such that the detector may be configured to detect imaging beams emitted by the first imaging source and the second imaging source.

In some embodiments, the radiation system may further include a third imaging source of a third type that is different from the first type of the first imaging source.

In some embodiments, the at least one detector may include one detector. The first imaging source, the second imaging source, and the third imaging source may share the detector such that the detector may be configured to detect imaging beams emitted by the first imaging source, the second imaging source, and the third imaging source.

In some embodiments, the second imaging source of the second type may be a DR imaging source.

In some embodiments, the third imaging source of the third type may be a DR imaging source.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 12 is a flowchart illustrating an exemplary imaging process of a radiation system according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by other expressions if they achieve the same purpose.

Figure 6:
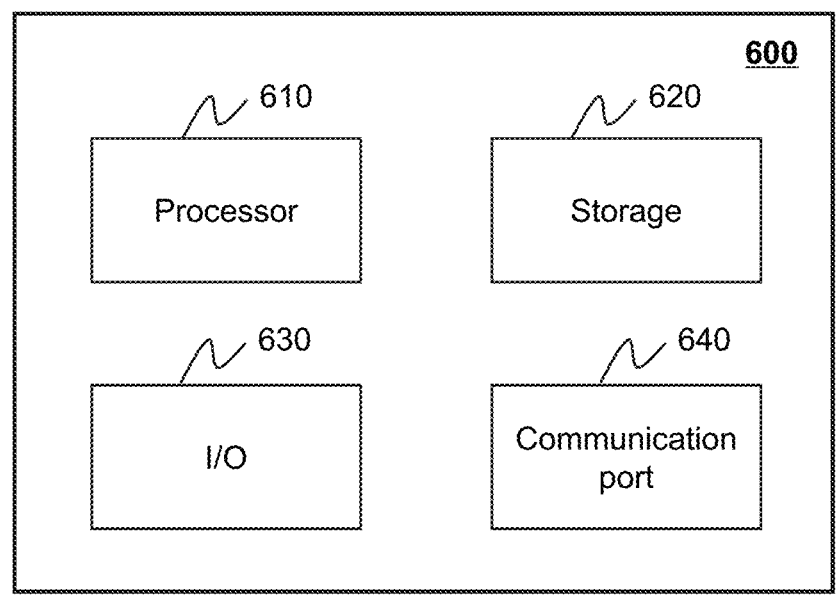
FIG. 6 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/ block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 610 as illustrated in FIG. 6) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

In this present disclosure, the terms "radiation therapy," "radiotherapy," "radiation treatment," "treatment," and "treatment session" may be used interchangeably to refer to a therapy for treating, e.g., cancers and other ailments in biological (e.g., human and animal) tissue using radiation. The terms "treatment plan," "therapy plan," and "radiotherapy plan" may be used interchangeably to refer to a plan used to perform radiotherapy.

An aspect of the present disclosure relates to a radiation system. The radiation system may include a gantry, a treatment head, a detector, and a plurality of imaging sources. The treatment head, the detector, and the plurality of imaging sources may be mounted on the gantry. The treatment head may be configured to deliver a treatment beam toward an object. The plurality of imaging sources may be configured to deliver a plurality of imaging beams toward the object. At least two of the plurality of imaging sources may share the detector. The detector (also referred to as an imaging beam detector) may be configured to detect at least two of the plurality of imaging beams. The detected at least two imaging beams may be emitted by different imaging sources of the at least two imaging sources.

According to some embodiments of the present disclosure, the at least two of the plurality of imaging sources may share the imaging beam detector such that there may be enough space to arrange the treatment head, the plurality of imaging sources, and the imaging beam detector in a same plane, thereby bringing about one or more the following benefits. The length (e.g., along the y-direction illustrated in FIG. 1) of the gantry may be reduced, thereby making it more convenient to transport and/or set up the radiation system, and/or reducing the space needed for housing the radiation system. Besides, since the treatment head and the plurality of imaging sources are located in the same plane, the object, or a portion thereof, may be imaged during a radiotherapy at a position where the object is treated, thereby obviating the need to move the object between different treatment and imaging positions and obviating the need to perform position adjustments with respect to a treatment plan of the object, which in turn may save time and improve the utilization efficiency of the radiation system, alleviate the problems of different table sagging of the patient support between different treatment and imaging positions and resultant errors in a treatment performed at a treatment position based on imaging performed at an imaging position, and allow in-treatment imaging to facilitate in-treatment monitoring or tracking of the object, or a portion thereof, and a timely adjustment of the treatment execution accordingly.

Another aspect of the present disclosure may relate to a radiation system. The radiation system may include a plurality of imaging sources and a detector (also referred to as an imaging beam detector, e.g., a curvilinear detector). At least two of the plurality of imaging sources may share the detector. The detector may be configured to detect at least two imaging beams emitted by the at least two imaging sources, respectively. The detected at least two imaging beams may be emitted by different imaging sources of the at least two imaging sources. The radiation system may generate a pre-treatment image (e.g., a 3D image) by causing the CT imaging source of the radiation system to emit a pre-treatment imaging beam toward an object. The radiation system may determine position information (e.g., a position, a contour) of a target region of the object based on the pre-treatment image and cause the target region of the object to be positioned in the radiation system according to the position information. In some embodiments, the radiation system may also use the pre-treatment image to determine a treatment plan of the target region of the object or determine whether to adjust a treatment plan determined based on a plan image of the object.

According to another aspect of the present disclosure, the radiation system may cause, based on a treatment plan of the object, a treatment head of the radiation system to deliver at least one treatment beam toward a target region of an object to perform a radiotherapy on the target region. The radiation system may also generate at least one treatment image based on at least a portion of the at least one treatment beam detected by a detector (also referred to as a treatment beam detector, e.g., an electronic portal imaging device (EPID)) of the radiation system. Before the radiotherapy of the target region, the radiation system may generate a pre-treatment image (e.g., a 3D image) by causing the CT imaging source of the radiation system to emit a pre-treatment imaging beam toward the object. Further, the radiation system may determine, based on the pre-treatment image and the at least one treatment image, whether a delivery of the treatment beam conforms to a planned treatment beam delivery according to the treatment plan. In some embodiments, the radiation system may estimate an actual radiation dose distribution (e.g., a 2D radiation dose distribution, a 3D radiation dose distribution) of the treatment beam in the object based on the at least one treatment image. The radiation system may determine a difference between the actual radiation dose distribution and a planned radiation dose distribution in the object and then determine, based on the difference, whether the treatment beam delivery conforms to the planned treatment beam delivery according to the treatment plan. In such cases, the radiation system may achieve an in-treatment monitoring by monitoring the actual radiation dose distribution in the object in (substantially) real-time during a treatment session. If it is determined that the actual radiation dose distribution deviates from the planned radiation dose distribution, the radiation system may adjust a delivery of the treatment beam or position information (e.g., a position thereof) of the target region accordingly, thereby improving the accuracy of the radiotherapy.

According to a further aspect of the present disclosure, the radiation system may cause a treatment head of the radiation system to deliver a treatment beam toward a target region of an object based on a treatment plan of the object to perform a radiotherapy on the target region. During the radiotherapy, the radiation system may generate a plurality of groups of images (e.g., a plurality of groups of 2D images) of the object, each group at a time point. A group of images may be obtained by causing the plurality of imaging sources of the radiation system to emit a plurality of imaging beams toward the object and the detector to provide views of the object at a time point from different directions/view angles. The radiation system may track, based on the plurality of groups of images, position information (e.g., a position thereof) of the object at different time points. If it is detected that a change of the position information of the target region exceeds a threshold, the radiation system may adjust a delivery of the treatment beam or position information (e.g., a position thereof) of the target region accordingly, thereby improving the accuracy of the radiotherapy.

Compared to images from one (e.g., from the view perpendicular to the direction of the motion of interest) or two views (e.g., two views one of which is perpendicular to the direction of the motion of interest), the plurality of images from different views of the object may provide anatomical and/or motion information of the target region of the object with improved quality for the monitoring, thereby improving the monitoring accuracy. For example, the plurality of imaging sources may include two DR imaging sources whose axes (e.g., axes 272 and 274 illustrated in FIG. 2A) are at an angle to each other (e.g., perpendicular to each other) and a CT imaging source, thereby providing three images from three different views of the object.

In some embodiments, the plurality of imaging beams may include a CT imaging beam emitted by the CT imaging source, and the CT imaging beam may be of a fan angle achieved by adjusting an aperture of a collimator of the CT imaging source. By adjusting the fan angle of the CT imaging source, the plurality of images may be 2D images generated without performing an image reconstruction process, reducing the time for image acquisition and processing to a relatively short time (e.g., 1 millisecond, 5 milliseconds, 10 milliseconds, 50 milliseconds, 100 milliseconds), thereby improving the tracking efficiency and/or allowing an in-treatment tracking/monitoring.

In some embodiments, a tomosynthesis (also referred to as digital tomosynthesis (DTS)) imaging may be performed by emitting the plurality of imaging beams by the plurality of imaging sources. Each of the plurality of imaging sources may only need to rotate within a relatively small angle range to perform the tomosynthesis imaging; that is, the imaging source only needs to rotate for a relatively short time period, thereby improving a temporal resolution of the tracking. In some embodiments, if each of the plurality of imaging sources rotates within a same angle range as that when only one imaging source performs the tomosynthesis imaging, a quality of an image generated by tomosynthesis imaging performed by the plurality of imaging sources may be improved compared to that of an image generated by tomosynthesis imaging performed by one imaging source.

According to another aspect of the present disclosure, the radiation system may cause the plurality of imaging sources of the radiation system to emit a plurality of imaging beams at least two of which are of different energy levels. The plurality of imaging beams may include a CT imaging beam emitted by the CT imaging source, and the CT imaging beam may be of a fan angle achieved by adjusting an aperture of a collimator of the CT imaging source. The radiation system may generate an image (e.g., a multi-energy image) of the object based on at least a part of the plurality of imaging beams of different energy levels detected by the detector. The radiation system may also generate a second image (e.g., a 3D image) by causing the CT imaging source to emit a second CT imaging beam of a second fan angle achieved by adjusting the aperture of the collimator of the CT imaging source. In some embodiments, the radiation system may generate a fused image by fusing the image and the second image. The fused image may have an improved contrast of tissues (e.g., soft tissues) in and/or surrounding the target region. The radiation system may determine information of the target region (e.g., a contour of the target region, a contour of a tissue in and/or surrounding the target region) in the fused image. In some embodiments, the radiation system may also adjust a treatment plan based on the information of the target region in the fused image. Further, a treatment beam may be accurately delivered to the target region based on the determined information of the target region and the treatment plan or the adjusted treatment plan during a treatment session of the target region, thereby reducing damages to an organ or tissue in the vicinity of the target region due to exposure to treatment radiation, and/or improving the efficacy of the radiotherapy.

In some embodiments, the second fan angle may be larger than the fan angle. By dynamically adjusting a fan angle of the CT imaging source, the radiation system may generate a 3D image with more anatomical information or a 2D image within a relatively short time, thereby improving the utilization efficiency of the radiation system with a minimal or acceptable compromise of the quality of the acquired images with respect to their intended use.

Figure 1:
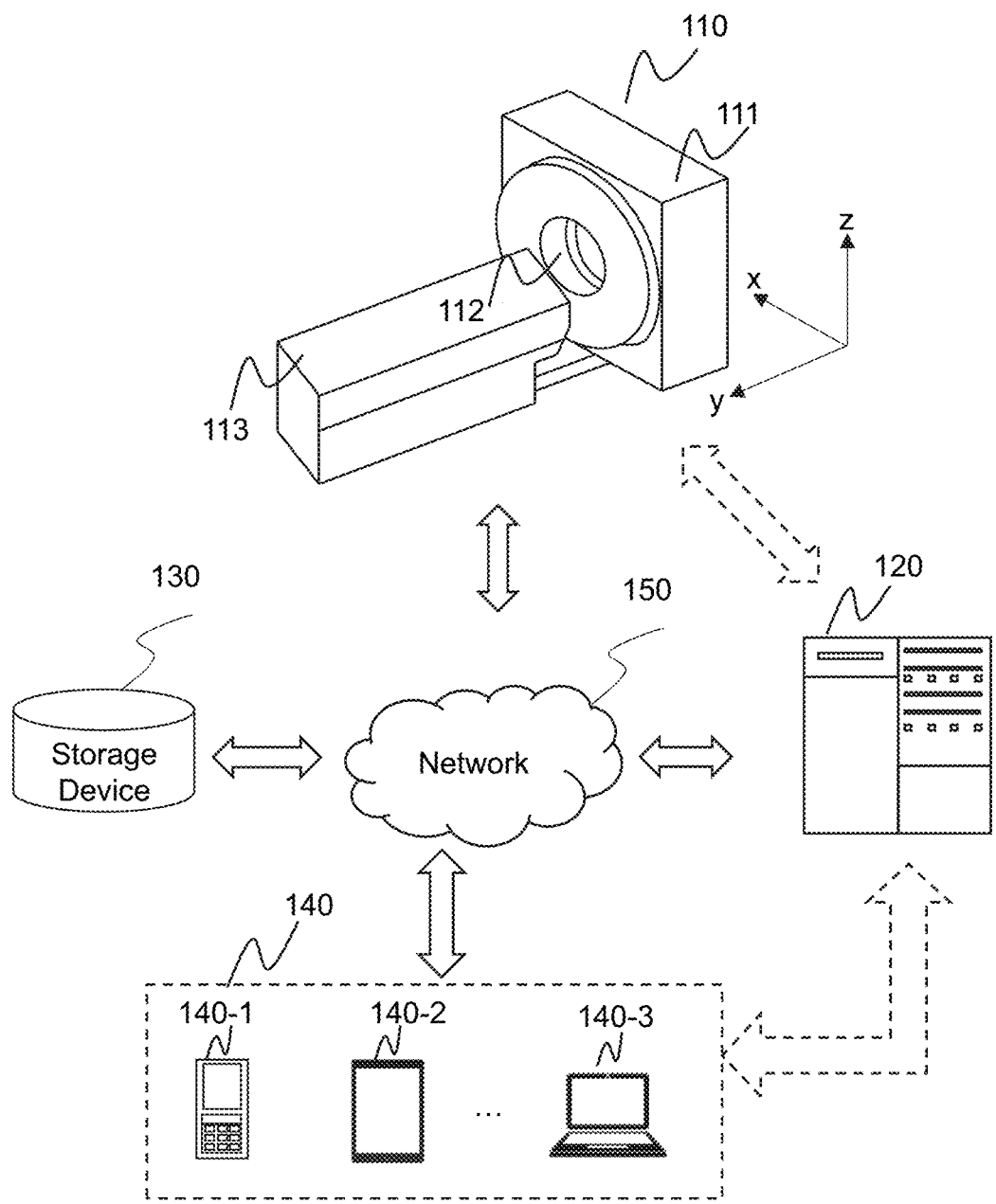
FIG. 1 is a schematic diagram illustrating an exemplary radiation system according to some embodiments of the present disclosure.

FIG. 1 is a schematic diagram illustrating an exemplary radiation system according to some embodiments of the present disclosure. In some embodiments, the radiation system 100 may be configured to provide radiation therapy (e.g., stereotactic radiosurgery and/or precision radiotherapy) for lesions, tumors, and conditions anywhere in a patient where radiation treatment is indicated. In some embodiments, the radiation system 100 may include a treatment plan system (TPS), an image-guided radiotherapy (IGRT) system, etc.

As illustrated in FIG. 1, the radiation system 100 may include a radiation device 110, a processing device 120, a storage device 130, one or more terminals 140, and a network 150. The components in the radiation system 100 may be connected in one or more of various ways. Merely by way of example, the radiation device 110 may be connected to the processing device 120 through the network 150. As another example, the radiation device 110 may be connected to the processing device 120 directly as indicated by the bi-directional arrow in dotted lines linking the radiation device 110 and the processing device 120. As a further example, the storage device 130 may be connected to the processing device 120 directly or through the network 150. As still a further example, the terminal 140 may be connected to the processing device 120 directly (as indicated by the bi-directional arrow in dotted lines linking the terminal 140 and the processing device 120) or through the network 150.

In some embodiments, the radiation system 100 may perform image-guided radiation therapy (IGRT) that monitors, using X-ray imaging, a target volume (also referred to as a target region, e.g., a tumor, a lesion, etc.) to be treated inside an object (e.g., a patient). In this case, the radiation device 110 may include a treatment assembly (also referred to as a treatment device) and an imaging assembly (also referred to as an imaging device). The treatment assembly may be configured to deliver a treatment beam to the target volume to perform a radiotherapy on the target volume. The imaging assembly may be configured to perform imaging (e.g., two-dimensional (2D) imaging, three-dimensional (3D) imaging, or four-dimensional (4D) imaging) on the target volume and/or normal tissue surrounding the target volume (also referred to as "organ at risk") before, after, or while the radiotherapy is performed. In this way, the anatomy, as well as the motion or deformation, of the target volume can be detected, and the patient's position and/or the treatment beam can be adjusted for more precise radiation dose delivery to the target volume.

In some embodiments, the imaging assembly may include a plurality of imaging sources and a detector (also referred to as an imaging beam detector, e.g., a curvilinear detector). "Plurality" used herein may refer to two or more. The plurality of imaging sources may be configured to deliver a plurality of imaging beams toward the object. In some embodiments, at least two of the plurality of imaging sources may share the detector. The detector may be configured to detect at least two imaging beams emitted by the at least two of the plurality of imaging sources. The detected at least two imaging beams may be emitted by different imaging sources of the at least two imaging sources. A detection range of the detector may encompass an aggregate field of view (FOV) of the at least two of the plurality of imaging sources. In some embodiments, the at least two imaging sources may be all the plurality of imaging sources, and the detection range of the detector may encompass an aggregate FOV of the plurality of imaging sources. In some embodiments, the at least two imaging sources may be a portion of the plurality of imaging sources, the detection range of the detector may encompass an aggregate FOV of the portion of the plurality of imaging sources. In some embodiments, an imaging dataset or an image generated based on the detected at least two imaging beams may be used to monitor the object (e.g., a motion thereof). A width (e.g., along the y-direction illustrated in FIG. 1) of the detector may be large enough to ensure that the imaging dataset or the image contains enough anatomical and/or motion information of the target region, thereby achieving a desired monitoring accuracy. In some embodiments, the width of the detector may exceed a threshold (e.g., 10 centimeters). For example, the width of the detector may be 16 centimeters.

In some embodiments, the plurality of imaging sources may include at least one (e.g., one, two) computed tomography (CT) imaging source and at least one (e.g., two, three) digital radiography (DR) imaging source. For example, the plurality of imaging sources may include a CT imaging source and two DR imaging sources. In some embodiments, the detector may be configured to detect imaging beams emitted by the CT imaging source and the two DR imaging sources. The detection range of the detector may encompass an aggregate FOV of multiple imaging sources (e.g., the CT imaging source and the two DR imaging sources in the exemplary configuration described above) of the plurality of imaging sources.

In some embodiments, the detector may be configured to detect two imaging beams emitted by the two DR imaging sources, while the radiation system may include an additional detector configured to detect an imaging beam emitted by the CT imaging source, in which the additional detector may be positioned on a gantry 111 or outside the gantry 111. For example, the additional detector may be mounted on a first rotation ring of the plurality of imaging sources or a second rotation ring different from the first rotation ring. In some embodiments, the detection range of the detector may encompass an aggregate FOV of multiple imaging sources (e.g., the two DR imaging sources in the exemplary configuration described above) of the plurality of imaging sources.

In some embodiments, the detector may be configured to detect imaging beams emitted by the CT imaging source and one of the two DR imaging sources (also referred to as a first DR imaging source), while the radiation system may include an additional detector configured to detect an imaging beam from the other of the two DR imaging sources, in which the additional detector may be positioned on the gantry 111 or outside the gantry 111. For example, the additional detector may be mounted on a first rotation ring of the plurality of imaging sources or a second rotation ring different from the first rotation ring. In some embodiments, the detection range of the detector may encompass an aggregate field of view (FOV) of the multiple imaging sources (e.g., the CT imaging source and the first DR imaging source in the exemplary configuration described above) of the plurality of imaging sources.

In some embodiments, the imaging beam detector may include an anti-scatter grid configured to filter out a scattered portion of the plurality of imaging beams. The anti-scatter grid may be located between the object and the imaging beam detector. In some embodiments, an orientation (e.g., an angle thereof, a position thereof) of the anti-scatter grid may correspond to a direction of a non-scattering portion of the imaging beam (also referred to as CT imaging beam) emitted by the CT imaging source. The anti-scatter grid can filter out a corresponding scattered portion of the CT imaging beam without preventing a non-scattered portion of the CT imaging beam from being detected by the imaging beam detector. In some embodiments, at least a portion of the imaging beam detector may also be configured to detect an imaging beam (or referred to as a non-CT imaging beam) emitted by a non-CT imaging source (e.g., a DR imaging source) of the plurality of imaging sources other than the CT imaging source. Since a direction of such a non-CT imaging beam may be different from the direction of the CT imaging beam (e.g., as shown in FIG. 2A, FIG. 3, FIG. 4 or FIG. 5), the anti-scatter grid configured according to the direction of the CT imaging beam may fail to filter out a scattered portion of the non-CT imaging beam, and accordingly, at least a portion of the scattered portion of the non-CT imaging beam may be detected by the imaging beam detector. In order to solve the problems, the orientation of the anti-scatter grid may need to be adjusted.

In some embodiments, the anti-scatter grid may include a plurality of portions, an orientation of each of which may be adjustable relative to at least one of the plurality of imaging sources. An orientation of at least one of the plurality of portions of the anti-scatter grid that is configured to detect the non-CT imaging beam may be adjusted to correspond to the direction of the non-CT imaging beam. In some embodiments, the orientation of each of the plurality of portions of the anti-scatter grid may be adjusted based on a piezoelectric technology. Still take the plurality of imaging sources including the CT imaging source and the at least one DR imaging source as an example. An orientation of each of at least one portion of the plurality of portions of the anti-scatter grid may be adjustable relative to at least one of the at least one DR imaging source so that the orientation of at least one of the plurality of portions of the anti-scatter grid may be adjusted to correspond to a direction of at least one imaging beam when the at least one of the at least one DR imaging source emits the at least one corresponding imaging beam toward the object.

In some embodiments, the treatment assembly may include a treatment head 112. The treatment head 112 may be configured to deliver a treatment beam toward the object to perform a radiation treatment toward a target region inside the object and/or perform imaging on a region of interest (ROI) (e.g., including the target volume and/or organs at risk (OARs)) of the object. For example, the treatment head 112 may include at least one of an acceleration tube, a treatment source (e.g., an X-ray target), a primary collimator, a filter (e.g., a flattening filter), at least one jaw, a multi-leaf collimator (MLC), etc. In some embodiments, the treatment head 112 may include an acceleration tube of particles including, for example, photons, electrons, protons, or heavy ions, etc. In some embodiments, the treatment beam may include a relatively high energy beam (e.g., an MV beam). In some embodiments, the treatment beam may include a fan beam, a cone beam, or a tetrahedron beam.

In some embodiments, the treatment head 112, the plurality of imaging sources, and the detector (i.e., the imaging beam detector) may be mounted on the gantry 111 (e.g., an O-shaped gantry). For example, the detector may be fixedly mounted on the gantry 111. As another example, the plurality of imaging sources may be fixedly mounted on the gantry 111. In some embodiments, the treatment head 112, the plurality of imaging sources, and the detector may be located in a same plane. For example, the plane may be perpendicular to an axis (also referred to as a gantry axis) of the gantry 111 along the y-axis as illustrated in FIG. 1. The treatment head 112, the plurality of imaging sources, and the imaging beam detector may rotate with the gantry 111 or independently of the gantry 111. For example, the gantry 111 may include a rotatable roller. The treatment head, the imaging beam detector, and the plurality of imaging sources may be mounted on the rotatable roller and rotate with the rotatable roller.

In some embodiments, the plurality of imaging sources may rotate independently of the treatment head 112 or the gantry 111. For illustration purposes, at least one of the plurality of imaging sources and the imaging beam detector may be operably coupled to or mounted on a rotation ring other than the gantry 111. For example, the rotation ring may be inside the gantry 111. The at least one of the plurality of imaging sources and the imaging beam detector may rotate with the rotation ring. The rotation ring may be operably coupled to, mounted on, or separated from the gantry 111. The rotation ring may rotate with or independently of the gantry 111.

In some embodiments, the plurality of imaging sources and the imaging beam detector may be stationary or substantially stationary relative to each other. As used herein, two devices, e.g., two imaging sources, an imaging source and the imaging beam detector, being stationary relative to each other indicates that the relative positioning of the two devices stay unchanged regardless of whether at least one of the two devices moves with respect to the gantry 111 or the patient support 113.

In some embodiments, the treatment head 112 may synchronously rotate with the gantry to perform a coplanar radiotherapy on the object. During the coplanar radiotherapy, radiation beams emitted by the treatment head 112 at different time points may share a same geometric plane relative toward the object. In some embodiments, a non-coplanar radiotherapy may be performed on the object by tilting (e.g., with respect to the x-direction illustrated in FIG. 1,) the gantry or rotating the patient support 113 around the z-direction illustrated in FIG. 1. During the non-coplanar radiotherapy, radiation beams emitted by the treatment head 112 at different time points may be in different geometric planes.

In some embodiments, the plurality of imaging sources may include a CT imaging source and at least one DR imaging source. In some embodiments, an angle between an axis of an imaging beam emitted by the CT imaging source and an axis of the treatment beam emitted by the treatment head 112 may be within an angular range, for example, a range between 70 degrees and 110 degrees, a range between 80 degrees and 100 degrees, a range between 85 degrees and 95 degrees, a range between 40 degrees and 120 degrees, a range between 30 degrees and 130 degrees, etc. Merely by way of example, the angle between the axis of the imaging beam emitted by the CT imaging source and the axis of the treatment beam emitted by the treatment head 112 may be (substantially) 90 degrees, e.g., 90°+10°. As another example, the angle between the axis of the imaging beam emitted by the CT imaging source and the axis of the treatment beam emitted by the treatment head 112 may be smaller than 90 degrees.

In some embodiments, an angle between the axis of the treatment beam emitted by the treatment head 112 and an axis of the detector passing a center (e.g., a point 280 illustrated in FIGS. 2A and 2B) of the detector may be within an angular range, for example, a range between 70 degrees and 110 degrees, a range between 85 degrees and 95 degrees, a range between 50 degrees and 110 degrees, a range between 40 degrees and 120 degrees, a range between 30 degrees and 130 degrees, etc. The axis of the detector may refer to an axis linking the center of the gantry 111 in a plane where the detector is located and the center of the detector. Merely by way of example, the axis of the imaging beam emitted by the CT imaging source may be perpendicular to the detector at the center of the detector; that is, the angle between the axis of the treatment beam emitted by the treatment head 112 and the axis of the detector may be (substantially) 90 degrees, e.g., 90°+10°.

In some embodiments, the detector may include a plurality of detecting units arranged in at least one row and at least one column. The center of the detector may refer to a detecting unit at an intersection of the at least one row and the at least one column. For instance, the center of the detector may refer to a detecting unit located on an intersection of the central row and the center column of the plurality of detecting units of the detector.

In some embodiments, the at least one DR imaging source may include at least two DR imaging sources. An angle between axes of two imaging beams emitted by two of the at least two DR imaging sources may be within an angular range, for example, a range between 70 degrees and 110 degrees, a range between 80 degrees and 100 degrees, a range between 85 degrees and 95 degrees, a range between 40 degrees and 120 degrees, a range between 30 degrees and 130 degrees, etc. Merely by way of example, the at least one DR imaging source may include two DR imaging sources. An angle between axes of two imaging beams emitted by the two DR imaging sources may be (substantially) 90 degrees e.g., 90°+10°. It should be noted that a count of the at least one DR imaging source may be non-limiting, for example, one, two, three, four, five, etc.

In some embodiments, each of the plurality of imaging beams may cover an imaging region. The treatment beam may cover a treatment region. The plurality of imaging sources and the treatment head 112 may be configured such that the treatment region and the plurality of imaging regions may at least partially overlap. In some embodiments, a target region (e.g., a region to be treated) of the object may be placed in an overlapping region of the treatment region and the plurality of imaging regions.

In some embodiments, the treatment head 112 and at least one of the plurality of imaging sources may be configured to emit radiation beams alternately. For example, the at least one of the plurality of imaging sources may be configured to emit at least one imaging beam when a delivery of the treatment beam toward the object is paused. In some embodiments, the treatment head 112 and the plurality of imaging sources may be positioned to move within a same rotation ring. The at least one of the plurality of imaging sources may be able to move within a range of 360 degrees of the rotation ring for one time or repeatedly.

In some embodiments, the treatment head 112 and at least one of the plurality of imaging sources may be configured to emit radiation beams concurrently. For example, the at least one of the plurality of imaging sources may be configured to emit at least one imaging beam while the treatment head 112 is delivering the treatment beam. In some embodiments, the treatment head 112 and the plurality of imaging sources may be positioned to move within a same rotation ring. The at least one of the plurality of imaging sources may be able to move independently in a limited range less than 360 degrees of the rotation ring without interfering with the treatment beam for one time or repeatedly.

In some embodiments, the treatment assembly may include a detector (also referred to as a treatment beam detector) configured to detect the treatment beam emitted by the treatment head 112 and/or at least a portion of the imaging beam(s) emitted from the plurality of imaging sources. For example, the treatment beam detector may include an electronic portal imaging device (EPID). In some embodiments, the treatment beam detector may be stationary. In some embodiments, the treatment beam detector may move independently of the treatment head 112. In some embodiments, the treatment beam detector may be positioned diametrically opposite to the treatment head 112 and rotate with the treatment head 112. In some embodiments, the treatment beam detector may be configured to detect kV beams and also MV beams. In some embodiments, the treatment beam detector may be configured to detect kV beams only or MV beams only. More descriptions of the radiation device 110 may be found elsewhere in the present disclosure (e.g., descriptions in connection with FIGS. 2A-5).

In some embodiments of the present disclosure, the radiation system 100 may include the gantry 111, the treatment head 112, a plurality of imaging sources, and at least one detector. The treatment head 112 may be configured to deliver a treatment beam toward the object. The plurality of imaging sources may be configured to deliver a plurality of imaging beams toward the object. The at least one detector may be configured to detect a plurality of imaging beams emitted by the plurality of imaging sources. In some embodiments, the plurality of imaging sources may include a first imaging source of a first type and a second imaging source of a second type that is different from the first type. For example, the first imaging source of the first type may be a CT imaging source, and the second imaging source of the second type may be a DR imaging source.

In some embodiments, the at least one detector and the plurality of imaging sources may be mounted on the gantry. The plurality of imaging beams and the treatment beam may traverse a same plane of the object. In some embodiments, the at least one detector may include one detector. The first imaging source and the second imaging source may share the detector such that the detector may be configured to detect imaging beams emitted by the first imaging source and the second imaging source.

In some embodiments, the radiation system 100 may also include a third imaging source of a third type that is different from the first type. For example, the third imaging source of the third type may be the DR imaging source. In some embodiments, the at least one detector may include one detector. The first imaging source, the second imaging source, and the third imaging source may share the detector such that the detector may be configured to detect imaging beams emitted by the first imaging source, the second imaging source, and the third imaging source.

In the present disclosure, the x-axis, the y axis, and the z-axis shown in FIG. 1 may form an orthogonal coordinate system. The x-axis and the y axis shown in FIG. 1 may be horizontal, and the z-axis may be vertical. As illustrated, the positive x-direction along the x-axis may be from the right side to the left side of the radiation device 110 seen from the direction facing the front of the radiation device 110; the positive z-direction along the z-axis shown in FIG. 1 may be from the lower part to the upper part of the radiation device 110; the positive y-direction along the y axis shown in FIG. 1 may refer to a direction in which an object is moved out of a bore of the radiation device 110.

In some embodiments, the radiation device 110 may include the gantry 111 and a patient support 113. In some embodiments, the gantry 111 may be configured to support at least one of the treatment head 112, the plurality of imaging sources, the imaging beam detector, or the treatment beam detector. The gantry 111 may be configured to rotate around an object (e.g., a patient, or a portion thereof) that is moved into or located within a field of view (FOV)

(e.g., a region covered by at least one radiation beam emitted from at least one of the treatment head 112 or the plurality of imaging sources) of the radiation device 110. In some embodiments, the patient support 113 may be configured to support the object. The patient support 113 may have 6 degrees of freedom, for example, three translational degrees of freedom along three coordinate directions (i.e., x-direction, y-direction, and z-direction) and three rotational degrees of freedom around the three coordinate directions. Accordingly, the patient support 113 may move the object along a direction of the 3D coordinate system. Merely by way of example, the patient support 113 may move the object into the FOV of the radiation device 110 along the y-direction in FIG. 1.

In some embodiments, the object may be biological or non-biological. Merely by way of example, the object may include a patient, a man-made object, etc. As another example, the object may include a specific portion, organ, and/or tissue of the patient. For example, the object may include head, brain, neck, body, shoulder, arm, thorax, cardiac, stomach, blood vessel, soft tissue, knee, feet, or the like, or any combination thereof. In the present disclosure, "subject" and "object" are used interchangeably.

The network 150 may facilitate exchange of information and/or data. In some embodiments, one or more components of the radiation system 100 (e.g., the radiation device 110, the processing device 120, the storage device 130, or the terminal 140) may send information and/or data to another component(s) in the radiation system 100 via the network 150. For example, the processing device 120 may obtain a user instruction from the terminal 140 via the network 150. As another example, the processing device 120 may obtain scan data (e.g., projection data) from the radiation device 110 via the network 150. In some embodiments, the network 150 may be any type of wired or wireless network, or combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired or wireless network access points such as base stations and/or internet exchange points through which one or more components of the radiation system 100 may be connected to the network 150 to exchange data and/or information.

The terminal 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 140 may remotely operate the radiation device 110. In some embodiments, the terminal 140 may operate the radiation device 110 via a wireless connection. In some embodiments, the terminal 140 may receive information and/or instructions inputted by a user, and send the received information and/or instructions to the radiation device 110 or to the processing device 120 via the network 150. In some embodiments, the terminal 140 may receive data and/or information from the processing device 120. In some embodiments, the terminal 140 may be part of the processing device 120. In some embodiments, the terminal 140 may be omitted.

In some embodiments, the processing device 120 may process data obtained from the radiation device 110, the storage device 130, or the terminal 140. For example, the processing device 120 may obtain projection data of an object from the radiation device 110 and generate an image of the object based on the projection data. As another example, the processing device 120 may cause one or more components (e.g., a treatment head, an imaging source, a detector, a collimator, a patient support, a gantry, etc.) of the radiation device 110 to be located at a specific position. The processing device 120 may be a central processing unit (CPU), a digital signal processor (DSP), a system on a chip (SoC), a microcontroller unit (MCU), or the like, or any combination thereof.

In some embodiments, the processing device 120 may be a single server or a server group. The server group may be centralized or distributed. In some embodiments, the processing device 120 may be local or remote. For example, the processing device 120 may access information and/or data stored in the radiation device 110, the storage device 130, and/or the terminal 140 via the network 150. As another example, the processing device 120 may be directly connected to the radiation device 110, the storage device 130, and/or the terminal 140, to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data and/or instructions. In some embodiments, the storage device 130 may store data obtained from the terminal 140 and/or the processing device 120. For example, the storage device 130 may store one or more images generated by the processing device 120. In some embodiments, the storage device 130 may store data and/or instructions that the processing device 120 may execute or use to perform exemplary methods described in the present disclosure. For example, the storage device 130 may store instructions that the processing device 120 may execute or use to generate one or more images based on projection data. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more components of the radiation system 100 (e.g., the radiation device 110, the processing device 120, the terminal 140). One or more components of the radiation system 100 may access the data or instructions stored in the storage device 130 via the network 150. In some embodiments, the storage device 130 may be directly connected to or communicate with one or more components of the radiation system 100 (e.g., the processing device 120, the terminal 140). In some embodiments, the storage device 130 may be part of the processing device 120.

Figure 2A:
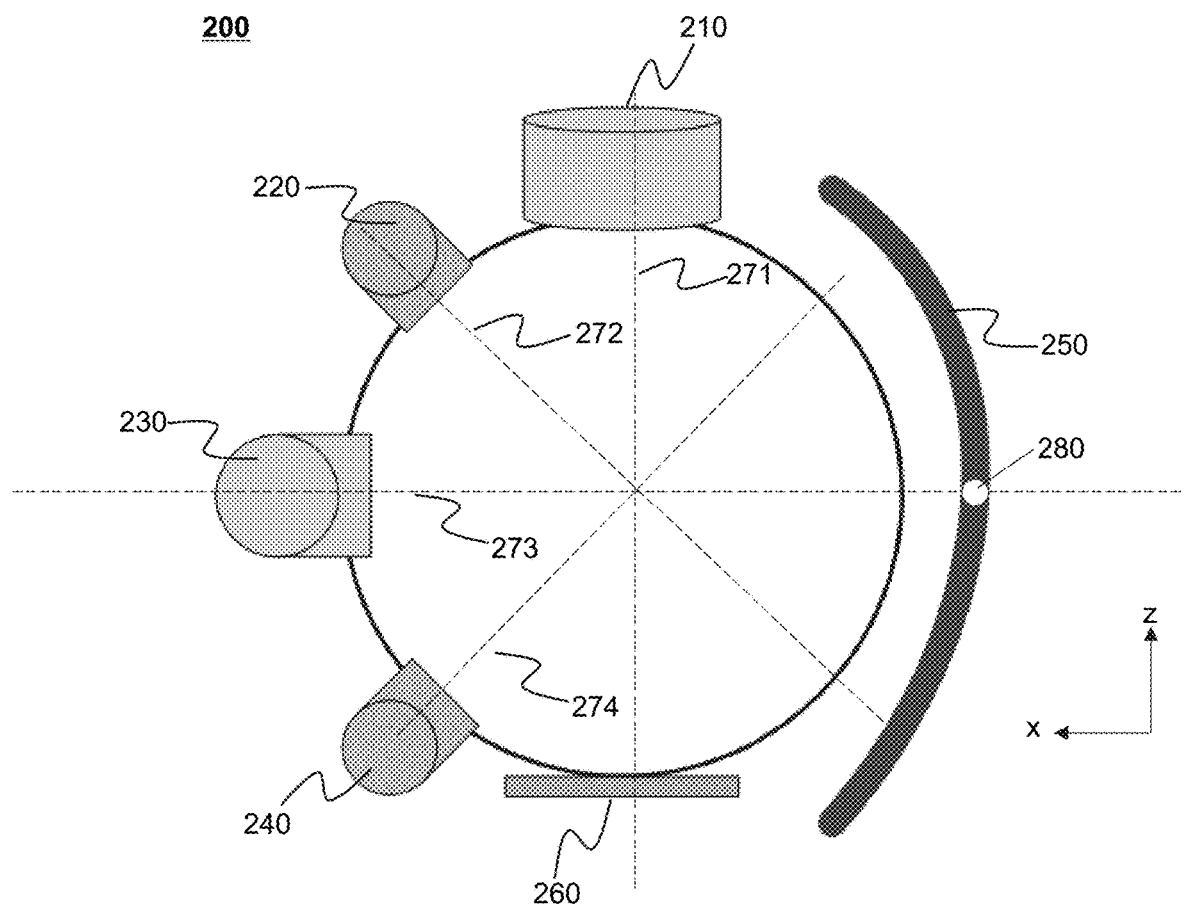
FIG. 2A is a schematic diagram illustrating an exemplary configuration of a radiation device according to some embodiments of the present disclosure.
Figure 2B:
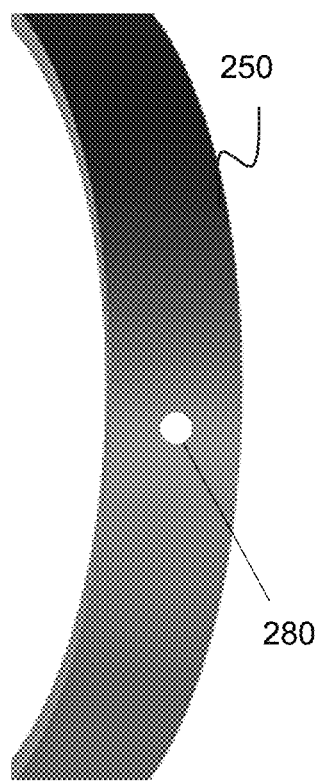
FIG. 2B is a schematic diagram illustrating an exemplary imaging beam detector according to some embodiments of the present disclosure.

FIG. 2A is a schematic diagram illustrating an exemplary configuration of a radiation device according to some embodiments of the present disclosure. FIG. 2B is a schematic diagram illustrating an exemplary imaging beam detector according to some embodiments of the present disclosure.

According to the configuration 200 shown in FIG. 2A, the radiation device 110 may include a treatment head 210, a first DR imaging source 220, a CT imaging source 230, a second DR imaging source 240, a first detector 250 (also referred to as an imaging beam detector), and a second detector 260 (also referred to as a treatment beam detector). The CT imaging source 230 may be located between the first DR imaging source 220 and the second DR imaging source 240. The first DR imaging source 220, the CT imaging source 230, and the second DR imaging source 240 may share the first detector 250. In some embodiments, a detection range of the first detector 250 (e.g., a curvilinear detector illustrated in FIGS. 2A and 2B) may encompass an aggregate FOV of the first DR imaging source 220, the CT imaging source 230, and the second DR imaging source 240. The first detector 250 may be configured to detect at least one imaging beam (e.g., a KV beam) emitted by at least one of the first DR imaging source 220, the CT imaging source 230, or the second DR imaging source 240. For example, the first detector 250 may detect imaging beams emitted by the first DR imaging source 220, the CT imaging source 230, and the second DR imaging source 240. The second detector 260 (e.g., an EPID) may be configured to detect a treatment beam emitted by the treatment head 210. In some embodiments, the second detector 260 may be configured to detect kV beams and also MV beams. In some embodiments, the second detector 260 may be configured to detect kV beams only or MV beams only.

In some embodiments, the radiation device 200 may be configured such that a region the at least one imaging beam traverses may partially overlap a region the treatment beam traverses in an overlapping region. An object (e.g., a patient) may be positioned such that a target region (e.g., a region to be imaged or treated) of the object is located within the overlapping region.

As shown in FIG. 2A, the treatment head 210, the first DR imaging source 220, the CT imaging source 230, the second DR imaging source 240, the first detector 250, and the second detector 260 may be located in a same plane. For example, the plane may be perpendicular to a gantry axis (e.g., a center axis thereof along the y-direction) of a gantry of the radiation device 110. An angle between axes 272 and 274 of two imaging beams emitted by the first DR imaging source 220 and the second DR imaging source 240 may be 90 degrees. An angle between an axis 273 of an imaging beam emitted by the CT imaging source 230 and an axis 271 of the treatment beam emitted by the treatment head 210 may be 90 degrees. The axis 273 may be perpendicular to the first detector 250 at a center (e.g., the point 280 illustrated in FIGS. 2A and 2B) of the first detector 250.

Figure 3:
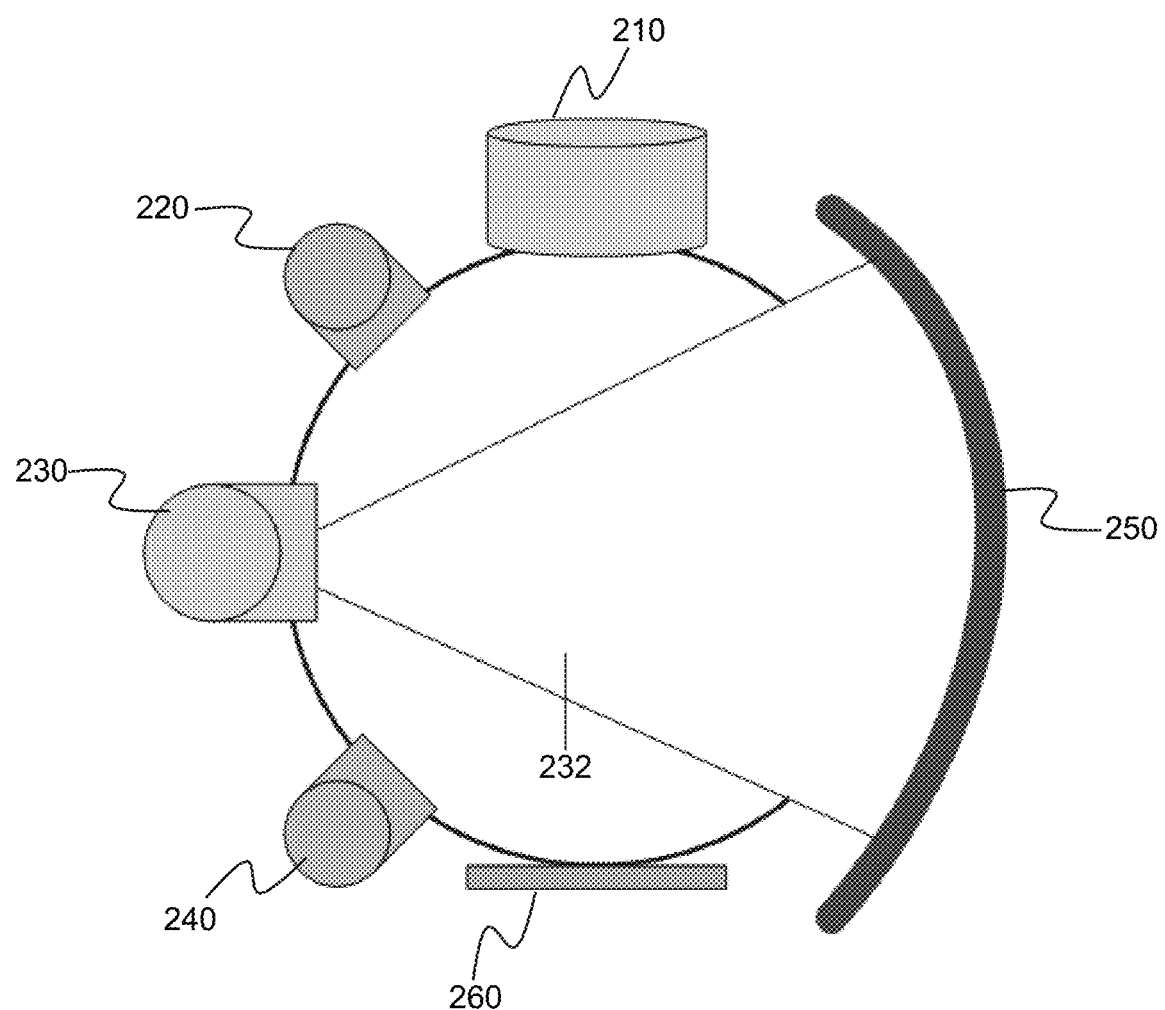
FIGS. 3-5 are schematic diagrams illustrating exemplary configurations of a radiation device according to some embodiments of the present disclosure.

FIG. 3 is a schematic diagram illustrating an exemplary configuration of a radiation device according to some embodiments of the present disclosure. As shown in the configuration 300, the radiation device 110 may include the treatment head 210, the first DR imaging source 220, the CT imaging source 230, the second DR imaging source 240, the first detector 250, and the second detector 260 illustrated in FIG. 2A.

According to the configuration 300, the CT imaging source 230 may be controlled to emit an imaging beam 232 toward an object. In some embodiments, the imaging beam 232 may have a relatively large fan angle. For example, the radiation range of the imaging beam 232 may be a maximum fan angle of an imaging beam emitted by the CT imaging source 230. As used herein, a fan angle of a radiation beam (e.g., the imaging beam 232) refers to an angular spread of the radiation beam emitted by a source and in a predetermined plane (e.g., a rotation plane) of the source when the source is stationary.

In some embodiments, the CT imaging source 230 may rotate or oscillate (rotating by an angle in opposite directions back and forth in an imaging scan) by a rotation angle with respect to the treatment head 210 while the imaging beam 232 is being emitted. The radiation range of the CT imaging source 230 may be a sum of the fan angle and the rotation angle. An imaging dataset corresponding to the imaging beam 232 of the radiation range (e.g., the sum of the fan angle and the rotation angle) can be used to generate a 3D image.

In some embodiments, an imaging dataset may be generated based on at least a portion of the imaging beam 232 detected by the first detector 250. Further, an image (e.g., a 3D image) may be generated based on at least a portion of the imaging dataset. In some embodiments, the image may be used to determine a treatment plan of a radiotherapy of the object or adjust a treatment plan determined based on a plan image of the object and/or monitor a radiotherapy of the object. More descriptions of determining the treatment plan, adjusting the treatment plan, and/or monitoring the radiotherapy based on the image may be found elsewhere in the present disclosure, for example, FIGS. 8-12 and the descriptions thereof.

Figure 4:
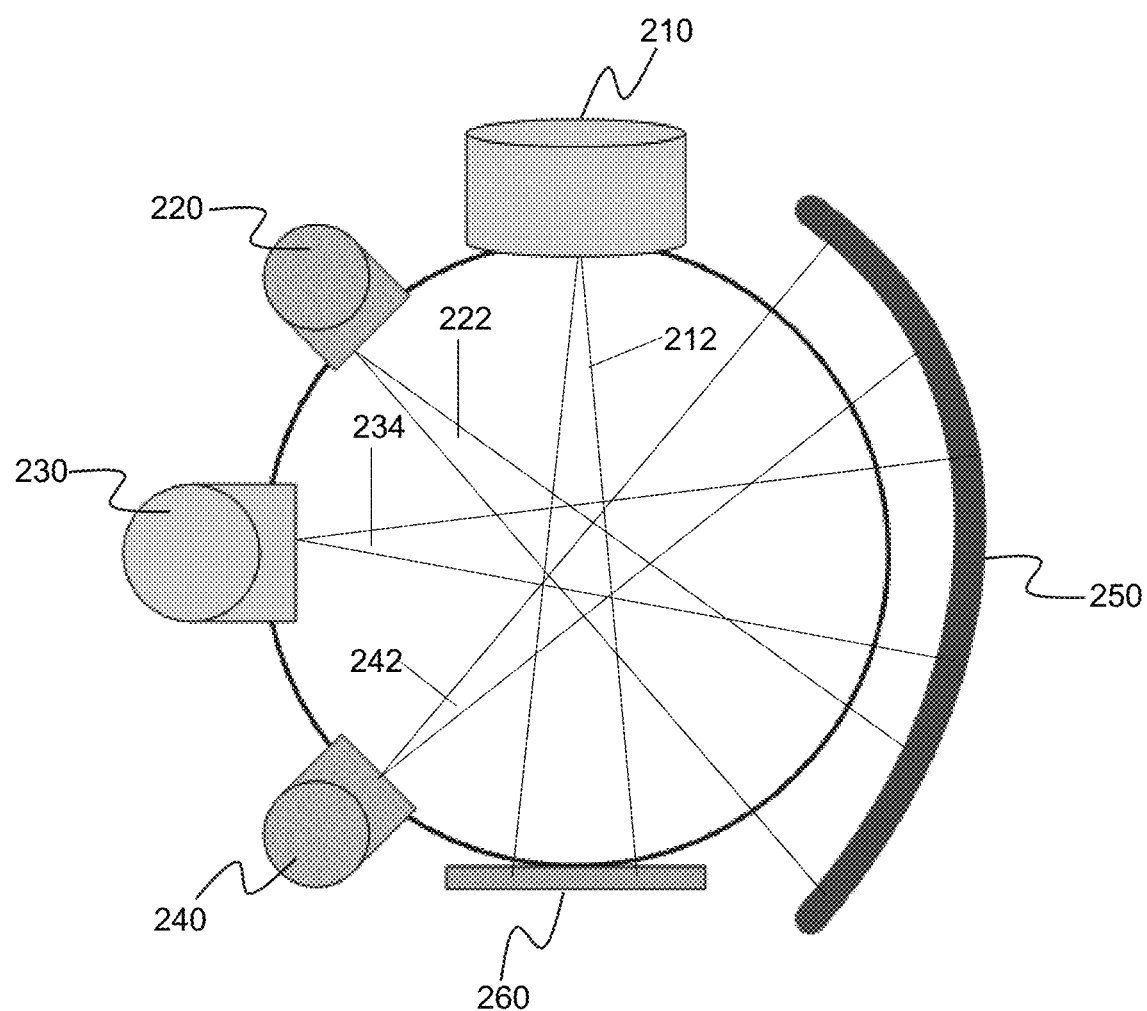

FIG. 4 is a schematic diagram illustrating an exemplary configuration of a radiation device according to some embodiments of the present disclosure. As shown in the configuration 400, the radiation device 110 may include the treatment head 210, the first DR imaging source 220, the CT imaging source 230, the second DR imaging source 240, the first detector 250, and the second detector 260 illustrated in FIG. 2A or FIG. 3.

According to the configuration 400, the treatment head 210 may be controlled to emit a treatment beam 212 toward a target region (e.g., a region to be treated) of an object. The treatment beam may be delivered toward the target region to perform a radiotherapy on the target region. The first DR imaging source 220, the CT imaging source 230, and the second DR imaging source 240 may be controlled to emit imaging beams 222, 234, and 242 toward the object, respectively. As used herein, a first fan angle of the imaging beam 234 may be smaller than or equal to a second fan angle of the imaging beam 232, in which the imaging beam 232 is delivered by the CT imaging source 230 when the first DR imaging source 220 and the second DR imaging source 240 are not emitting imaging beams, while the imaging beam 234 is delivered by the CT imaging source 230 when at least one of the first DR imaging source 220 or the second DR imaging source 240 are emitting imaging beams.

In some embodiments, the radiation device 110 may include a collimator configured to adjust a fan angle of an imaging beam emitted by a corresponding imaging source (e.g., the CT imaging source). The collimator may be positioned on an imaging beam pathway of the imaging beam. The imaging beam 232 or the imaging beam 234 may be generated by adjusting an aperture of the collimator, through which a portion of the imaging beam may be delivered toward the object and/or a portion of the imaging beam may be blocked by the collimator.

In some embodiments, a region the imaging beam 222, 234, and/or 242 traverses may partially overlap a region the treatment beam 212 traverses in an overlapping region. The object may be positioned such that a target region of the object is located within the overlapping region.

In some embodiments, the delivery of one or more imaging beams (e.g., the imaging beams 222, 234, and 242) may be concurrent with the delivery of the treatment beam 212. In some embodiments, the delivery of one or more imaging beams (e.g., the imaging beams 222, 234, and 242) and the delivery of the treatment beam 212 may alternate. That is, the imaging beams 222, 234, and 242) may be delivered when the treatment beam 212 is paused. In some embodiments, an imaging dataset may be generated based on each of the imaging beams 222, 234, and 242 detected by the first detector 250. In some embodiments, an image (e.g., a 2D image) may be generated for each of the imaging datasets. For example, a first image may be generated based on at least a portion of the imaging beam 234 detected by the first detector 250. A second image may be generated based on at least a portion of the imaging beam 222 detected by the first detector 250. A third image may be generated based on at least a portion of the imaging beam 242 detected by the first detector 250.

In some embodiments, each of the imaging beams 222, 234, and 242 may impinge on a detection region of the first detector 250. In some embodiments, the plurality of detection regions may be separate from each other. The sources of signals corresponding to the imaging beams 222, 234, and 242 that are detected by the first detector 250 may be distinguishable from each other based on where the signals are detected in the plurality of separated detection regions of the first detector 250. As used herein, the source of a signal corresponding an imaging beam detected by a detector refers to the imaging source that emits the imaging beam detected by the detector (e.g., the first detector 250) and results in the signal.

In some embodiments, at least two of the plurality of detection regions may at least partially overlap. In some embodiments, the imaging beams 222, 234, and 242 may be emitted at different time points such that the sources of signals corresponding to the imaging beams 222, 234, and 242 may be distinguishable from each other. In some embodiments, the sources of signals corresponding to the imaging beams 222, 234, and 242 that are detected by the first detector 250 may be distinguishable from each other using an anti-scatter grid located between the object and the first detector 250. In some embodiments, a detection region corresponding to the imaging beam 222 and a detection region corresponding to the imaging beam 234 may have an overlapping region. The sources of signals corresponding to the imaging beams 222 and 234 may be distinguishable by adjusting an orientation of at least a portion of the anti-scatter grid. For example, the orientation of the at least a portion of the anti-scatter grid may be adjusted to filter out a portion of the imaging beam 234 impinged on the overlapping region without preventing a portion of the imaging beam 222 from being detected by the first detector 250 to determine the source of signals corresponding to the imaging beam 222. As another example, the orientation of the at least a portion of the anti-scatter grid may be adjusted to filter out a portion of the imaging beam 222 impinged on the overlapping region without preventing a portion of the imaging beam 234 from being detected by the first detector 250 to determine the source of signals corresponding to the imaging beam 234.

In some embodiments, the imaging beams 222, 234, and 242 may be of a same energy level. In some embodiments, the imaging beams 222, 234, and 242 may be of different energy levels. A multi-energy image may be generated based on the first image, the second image, and the third image. At least one of the first image, the second image, the third image, or the multi-energy image may be used to determine a treatment plan of a radiotherapy of the object or adjust a treatment plan determined based on a plan image of the object and/or monitor a radiotherapy of the object. More descriptions of determining the treatment plan of the radiotherapy of the object or adjusting the treatment plan determined based on the plan image of the object and/or monitor the radiotherapy of the object may be found elsewhere in the present disclosure, for example, FIGS. 8-12, and the descriptions thereof.

Figure 5:
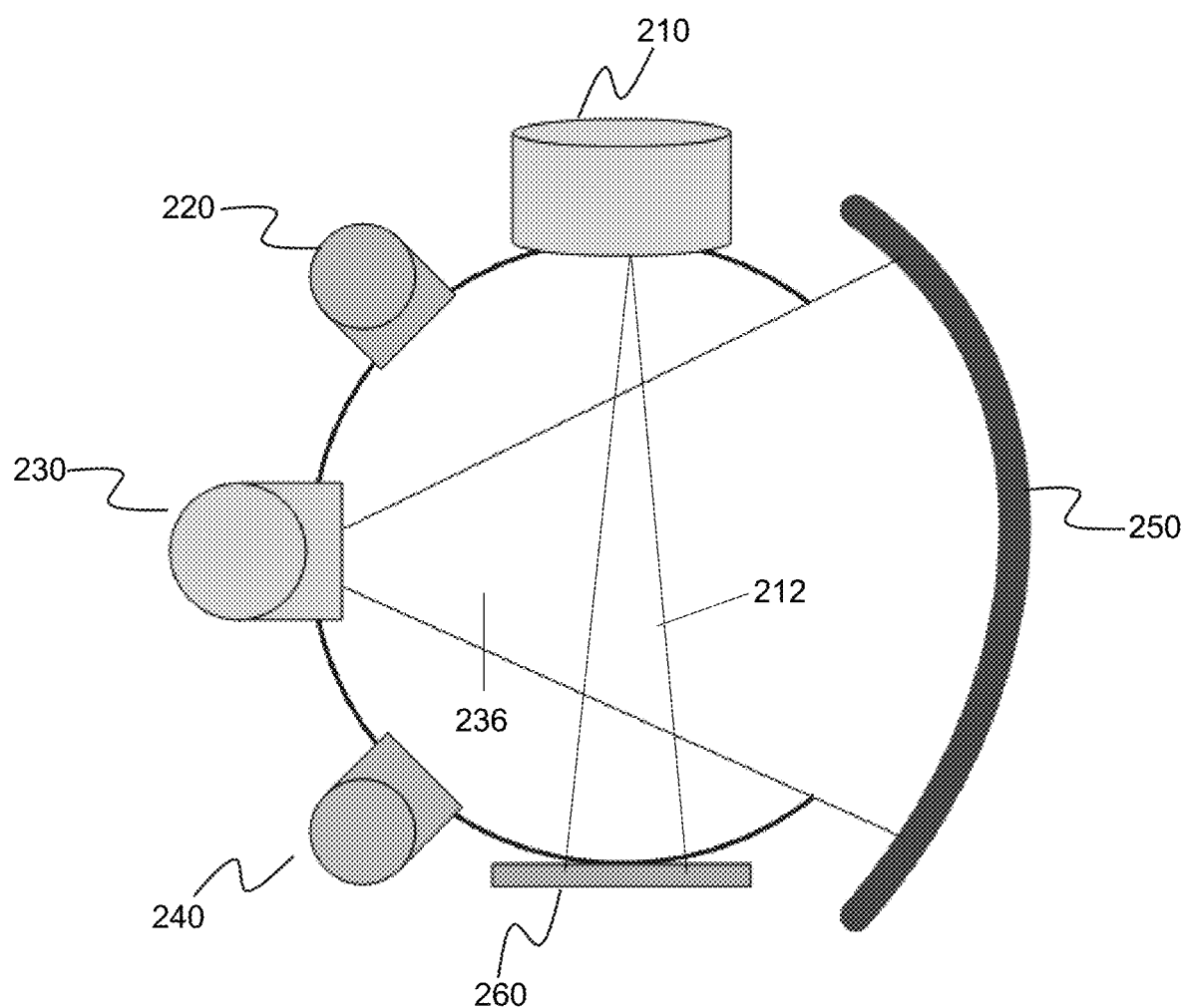

FIG. 5 is a schematic diagram illustrating an exemplary configuration of a radiation device according to some embodiments of the present disclosure. As shown in the configuration 500, the radiation device 110 may include the treatment head 210, the first DR imaging source 220, the CT imaging source 230, the second DR imaging source 240, the first detector 250, and the second detector 260 illustrated in FIGS. 2A-4.

According to the configuration 500, the CT imaging source 230 may be controlled to emit an imaging beam 236 toward an object. Similar to the imaging beam 232, the imaging beam 236 may have a relatively large fan angle. For example, the fan angle of the imaging beam 236 may be a maximum fan angle of an imaging beam emitted by the CT imaging source 230. In some embodiments, an imaging dataset may be generated based on at least a portion of the imaging beam 236 detected by the first detector 250. Further, a first image (e.g., a 3D image) may be generated based on the imaging dataset.

In some embodiments, the treatment head 210 may be controlled to emit a treatment beam 212 toward an object. The treatment beam may be delivered toward a target region of the object to perform a radiotherapy on the target region. A second image may be generated based on at least a portion of the treatment beam detected by the second detector 260. The region the imaging beam 236 traverses may partially overlap the region the treatment beam 212 traverses in an overlapping region. The object may be positioned such that a target region of the object is located within the overlapping region. In some embodiments, the first image and the second image may be used to monitor the execution of a treatment plan of a radiotherapy of the object, and/or a deviation of the execution from the treatment plan, or adjust a treatment plan determined based on a plan image of the object and/or monitor a radiotherapy of the object. More descriptions of determining the treatment plan of the radiotherapy of the object or adjust the treatment plan determined based on the plan image of the object and/or monitor the radiotherapy of the object may be found elsewhere in the present disclosure, for example, FIGS. 8-12 and the descriptions thereof.

FIG. 6 is a schematic diagram illustrating exemplary hardware and/or software components of a computing device on which the processing device 120 may be implemented according to some embodiments of the present disclosure. As illustrated in FIG. 6, the computing device 600 may include a processor 610, a storage 620, an input/output (I/O) 630, and a communication port 640.

The processor 610 may execute computer instructions (program code) and perform functions of the processing device 120 in accordance with techniques described herein. The computer instructions may include routines, programs, objects, components, signals, data structures, procedures, modules, and functions, which perform particular functions described herein. For example, the processor 610 may process data obtained from the radiation device 110, the storage device 130, the terminal 140, or any other component of the radiation system 100. In some embodiments, the processor 610 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 600. However, it should be noted that the computing device 600 in the present disclosure may also include multiple processors, thus operations and/or method steps that are performed by one processor as described in the present disclosure may also be jointly or separately performed by the multiple processors. For example, if in the present disclosure the processor of the computing device 600 executes both step A and step B, it should be understood that step A and step B may also be performed by two different processors jointly or separately in the computing device 600 (e.g., a first processor executes step A and a second processor executes step B, or the first and second processors jointly execute steps A and B).

The storage 620 may store data/information obtained from the radiation device 110, the storage device 130, the terminal 140, or any other component of the radiation system 100. In some embodiments, the storage 620 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 620 may store one or more programs and/or instructions to perform exemplary methods described in the present disclosure.

The I/O 630 may input or output signals, data, or information. In some embodiments, the I/O 630 may enable a user interaction with the processing device 120. For example, the processing device 120 may display an image through the I/O 630. In some embodiments, the I/O 630 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 640 may be connected to a network (e.g., the network 150) to facilitate data communications. The communication port 640 may establish connections between the processing device 120 and the radiation device 110, the storage device 130, or the terminal 140. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 640 may be a standardized communication port, such as RS232, RS485, etc. In some embodiments, the communication port 640 may be a specially designed communication port. For example, the communication port 640 may be designed in accordance with the digital imaging and communications in medicine (DICOM) protocol.

Figure 7:
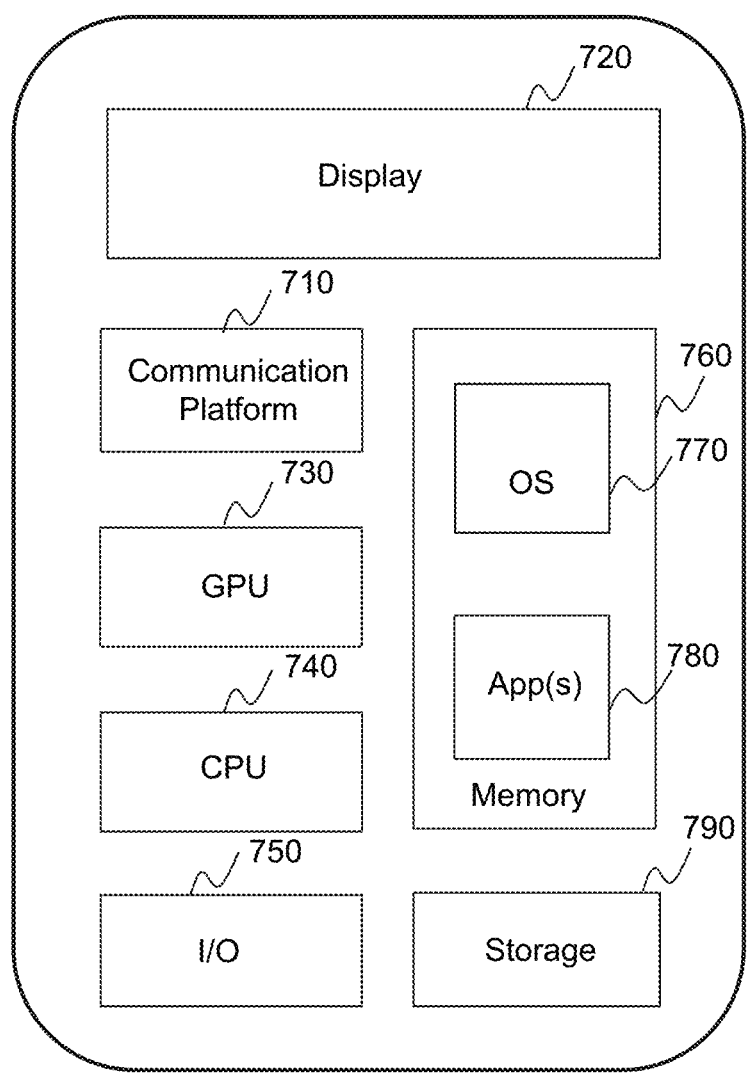
FIG. 7 is a schematic diagram illustrating exemplary hardware and/or software components of a mobile device according to some embodiments of the present disclosure.

FIG. 7 is a schematic diagram illustrating exemplary hardware and/or software components of a mobile device on which the terminal 140 may be implemented according to some embodiments of the present disclosure. As illustrated in FIG. 7, the mobile device 700 may include a communication platform 710, a display 720, a graphics processing unit (GPU) 730, a central processing unit (CPU) 740, an I/O 750, a memory 760, and a storage 790. In some embodiments, any other suitable component, including a system bus or a controller (not shown), may also be included in the mobile device 700. In some embodiments, a mobile operating system 770 (e.g., IOS, Android, Windows Phone, etc.) and one or more applications 780 may be loaded into the memory 760 from the storage 790 in order to be executed by the CPU 740. The applications 780 may include a browser or any other suitable mobile apps for receiving and rendering information relating to radiation therapy or other information from the processing device 120. User interactions with the information stream may be achieved via the I/O 750 and provided to the processing device 120 and/or other components of the radiation system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the radiation therapy as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 8:
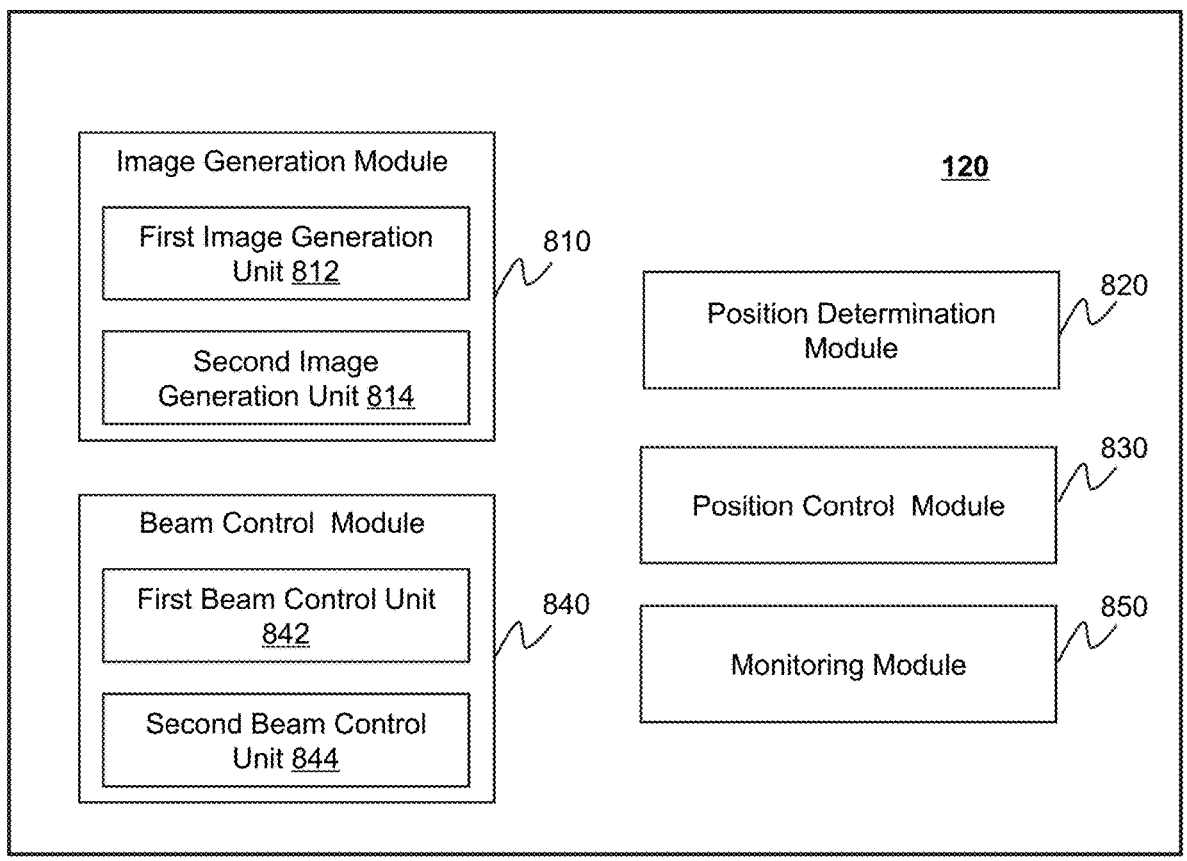
FIG. 8 is a block diagram illustrating an exemplary processing device according to some embodiments of the present disclosure.

FIG. 8 is a block diagram illustrating an exemplary processing device according to some embodiments of the present disclosure. The processing device 120 may include an image generation module 810, a position determination module 820, a position control module 830, a beam control module 840, and a monitoring module 850.

The image generation module 810 may be configured to generate at least one image of an object (e.g., a patient, a portion thereof). In some embodiments, the image generation module 810 may include a first image generation unit 812 and/or a second image generation unit 814.

The position determination module 820 may be configured to determine position information (e.g., a position thereof, a contour thereof) of a target region of the object in a radiation system based on at least one of the at least one image. In some embodiments, the processing device 120 may determine the position information of the target region using an image segmentation algorithm. The position control module 830 may be configured to cause the target region of the object to be positioned in the radiation system according to the position information.

The beam control module 840 may be configured to control a source (e.g., an imaging source, a treatment head of the radiation system) to emit a radiation beam (e.g., an imaging beam, a treatment beam) toward the object. In some embodiments, the beam control module 840 may include a first beam control unit 842 and/or a second beam control unit 844. The monitoring module 850 may be configured to monitor a treatment session of the object.

In some embodiments, the image generation module 810 (e.g., the image generation unit 812) may generate a pre-treatment image (e.g., a 3D image) by causing a CT imaging source of the radiation system to emit a pre-treatment imaging beam toward the object. The position determination module 820 may determine the position information of the target region of the object in the radiation system based on the pre-treatment image. The position control module 830 may cause the target region of the object to be positioned in the radiation system according to the position information. More descriptions regarding the functions of the modules described here may be found elsewhere in the present disclosure. See, e.g., FIG. 9 and the description thereof.

In some embodiments, the image generation module 810 (e.g., the imaging generation unit 812) may generate a pre-treatment image (e.g., a 3D image) by causing a CT imaging source of the radiation system to emit a pre-treatment imaging beam toward the object. The position control module 830 may cause the target region of the object to be positioned in the radiation system based on the pre-treatment image. The beam control module 840 (e.g., the first beam control unit 842) may cause the treatment head of the radiation system to deliver, based on a treatment plan of the object, at least one treatment beam toward the target region of the object. The image generation module 810 (e.g., the second image generation unit 814) may generate at least one treatment image based on at least a portion of the at least one treatment beam detected by a second detector of the radiation system. The monitoring module 850 may determine, based on the pre-treatment image and the at least one treatment image, whether a delivery of the treatment beam conforms to a planned treatment beam delivery according to the treatment plan. More descriptions regarding the functions of the modules described here may be found elsewhere in the present disclosure. See, e.g., FIG. 10 and the description thereof.

In some embodiments, the beam control module 840 (e.g., the first beam control unit 842) may cause the treatment head of the radiation system to deliver a treatment beam toward the target region of the object based on a treatment plan of the object. The beam control module 840 (e.g., the second beam control unit 844) may cause a plurality of imaging sources of the radiation system to emit a plurality of imaging beams toward the object and a detector (e.g., an imaging beam detector). The plurality of imaging beams may include a CT imaging beam emitted by the CT imaging source. The CT imaging beam may be of a fan angle achieved by adjusting an aperture of a collimator of the CT imaging source. The image generation module 810 (e.g., the first image generation unit 812) may generate a group of images (e.g., 2D images) of the object based on at least a part of the plurality of imaging beams detected by the detector. The position determination module 820 may determine position information of the target region based on the group of images of the object. More descriptions regarding the functions of the modules described here may be found elsewhere in the present disclosure. See, e.g., FIG. 11 and the description thereof.

In some embodiments, the beam control module 840 (e.g., the first beam control unit 842) may cause the plurality of imaging sources of the radiation system to emit a plurality of imaging beams of different energy levels toward the object and a detector (e.g., an imaging beam detector). The plurality of imaging beams may include a CT imaging beam emitted by the CT imaging source. The CT imaging beam may be of a fan angle achieved by adjusting an aperture of a collimator of the CT imaging source. The image generation module 810 (e.g., the first image generation unit 812) may generate an image of the object based on at least a part of the plurality of imaging beams of different energy levels detected by the detector. More descriptions regarding the functions of the modules described here may be found elsewhere in the present disclosure. See, e.g., FIG. 12 and the description thereof.

In some embodiments, the processing device 120 may be unnecessary to include all the modules and/or units described above, and the processing device 120 may only include a part of the modules and/or units. For example, the processing device 120 may include the image generation module 810, the position determination module 820, and the position control module 830. As another example, the processing device 120 may include the image generation module 810, the position control module 830, the beam control module 840, and the monitoring module 850. As a further example, the processing device 120 may include the image generation module 810, the position determination module 820, and the beam control module 840. As still a further example, the processing device 120 may include the image generation module 810 and the beam control module 840.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module. The storage module may be configured to store data generated during any process performed by any component of the processing device 120. As another example, each of the components of the processing device 120 may include a storage apparatus. Additionally or alternatively, the components of the processing device 120 may share a common storage apparatus.

Figure 9:
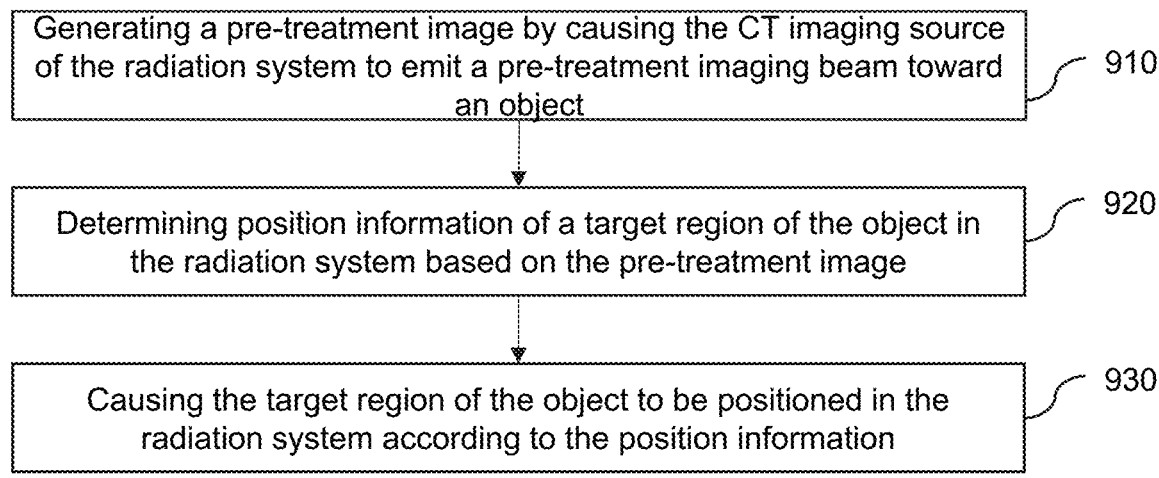
FIG. 9 is a flowchart illustrating an exemplary imaging process of a radiation system according to some embodiments of the present disclosure.

FIG. 9 is a flowchart illustrating an exemplary imaging process of a radiation system according to some embodiments of the present disclosure. The process 900 may be implemented in the radiation system 100 illustrated in FIG. 1. For example, the process 900 may be stored in the storage device 130 and/or the storage 620 in the form of instructions (e.g., an application), and invoked and/or executed by the processing device 120 (e.g., the processor 610 illustrated in FIG. 6, or one or more modules in the processing device 120 illustrated in FIG. 8). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In some embodiments, the radiation system may include a plurality of imaging sources and a detector (e.g., the imaging beam detector illustrated in FIGS. 1-5, e.g., a curvilinear detector). At least two of the plurality of imaging sources may share the detector. The detector may be configured to detect at least two imaging beams emitted by the at least two different imaging sources of the plurality of imaging sources. The detected at least two imaging beams may be emitted by different imaging sources of the at least two imaging sources. The radiation system may be similar to the radiation system 100 illustrated in FIGS. 1-5, the descriptions of which are not repeated here.

In 910, the processing device 120 (e.g., the image generation module 810, e.g., the first image generation unit 812) may generate a pre-treatment image (e.g., a 3D image) by causing the CT imaging source of the radiation system to emit a pre-treatment imaging beam toward an object (e.g., a patient, or a portion thereof). In some embodiments, the processing device 120 may obtain an imaging dataset (e.g., projection data) corresponding to at least a portion of the pre-treatment imaging beam detected by the detector (e.g., the imaging beam detector illustrated in FIGS. 1-5) of the radiation system. In some embodiments, the processing device 120 may generate the pre-treatment image based on at least a portion of the imaging dataset. In some embodiments, the processing device 120 may reconstruct the pre-treatment image using a reconstruction algorithm. For example, the reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

In some embodiments, the pre-treatment imaging beam may be of a fan angle achieved by adjusting an aperture of a collimator of the CT imaging source. In some embodiments, the CT imaging source may rotate or oscillate (rotating by an angle in opposite directions back and forth in an imaging scan) by a rotation angle with respect to a treatment head of the radiation system while the pre-treatment imaging beam is being emitted. The radiation range of the CT imaging source may be a sum of the fan angle and the rotation angle. An imaging dataset corresponding to the pre-treatment imaging beam of the radiation range (e.g., the sum of the fan angle and the rotation angle) can be used to generate a 3D image.

In some embodiments, a radiation device of the radiation system may have the configuration 300 in 910. As described in connection with FIG. 3, the radiation device may include the treatment head, two DR imaging sources, the CT imaging source and the imaging beam detector. The pre-treatment imaging beam may have a relatively large fan angle, in which the pre-treatment imaging beam is delivered by the CT imaging source when the two DR imaging sources are not emitting imaging beams.

In 920, the processing device 120 (e.g., the position determination module 820) may determine position information of a target region of the object in the radiation system based on the pre-treatment image. For example, the position information of the target region may include a position of the target region, a contour of the target region, etc. In some embodiments, the processing device 120 may determine the position information of the target region by segmenting the pre-treatment image using an image segmentation algorithm. For example, the image segmentation algorithm may include a thresholding algorithm, a clustering algorithm, a motion and interactive segmentation algorithm, a compression-based algorithm, a histogram-based algorithm, an edge detection algorithm, a region-growing algorithm, a model-based segmentation algorithm (e.g., a neural network model), or the like, or any combination thereof.

In 930, the processing device 120 (e.g., the position control module 830) may cause the target region of the object to be positioned in the radiation system according to the position information.

In some embodiments, the processing device 120 may generate a second pre-treatment image by causing at least one of the plurality of imaging sources to emit at least one second pre-treatment imaging beam toward the object. In some embodiments, the at least one second pre-treatment imaging beam may include at least two second pre-treatment imaging beams of a same energy level that are emitted by at least two of the plurality of imaging sources, respectively. In some embodiments, the at least one second pre-treatment imaging beam may include at least two second pre-treatment imaging beams of different energy levels that are emitted by at least two of the plurality of imaging sources, respectively.

For example, the second pre-treatment image may be a multi-energy image. In some embodiments, the at least one second pre-treatment imaging beam may include at least two second pre-treatment imaging beams that are of different energy levels. In some embodiments, the at least two second pre-treatment imaging beams of different energy levels may be emitted by at least two of the plurality of imaging sources of the radiation system. In some embodiments, the at least two second pre-treatment imaging beams of different energy levels may be emitted by one of the plurality of imaging sources that is configured to emit imaging beams of different energy levels. For example, the imaging source may emit the imaging beams of different energy levels by adjusting a voltage of the imaging source.

In some embodiments, the detector (e.g., a layer detector) may detect signals resulting from the second pre-treatment imaging beams impinging on the detector. The detector may determine the imaging sources by which the impinging imaging beams are emitted. More descriptions regarding the imaging source determination may be found elsewhere in the present disclosure. See, e.g., FIG. 4 and the description thereof.

In some embodiments, if the at least one imaging source includes the CT imaging source, the CT imaging source may be adjustably collimated by the collimator of the radiation system. A first fan angle of one of the at least one second pre-treatment imaging beam emitted by the CT imaging source may be smaller than or equal to a second fan angle of the pre-treatment imaging beam. The second pre-treatment imaging beam emitted by the CT imaging source may be of the second fan angle achieved by adjusting the aperture of the collimator of the CT imaging source.

The processing device 120 may generate the second pre-treatment image based on an imaging dataset corresponding to each of the at least two second pre-treatment imaging beams of different energy levels detected by the detector. For instance, the processing device 120 may generate at least two images (e.g., a 2D image) based on at least two imaging datasets corresponding to the at least two imaging beams and generate the second pre-treatment image by fusing the at least two images, e.g., according to a fusion algorithm. For example, the fusion algorithm may include an averaging algorithm, a Brovey algorithm, a principal component analysis (PCA) algorithm, or the like, or any combination thereof.

Further, the processing device 120 may adjust a treatment plan of the target region of the object based on the pre-treatment image and the second pre-treatment image. In some embodiments, the processing device 120 may generate a fused image by fusing the pre-treatment image and the second pre-treatment image. During the image fusion, detailed contour information of the target region and/or tissues (e.g., soft tissues) surrounding the target region may be extracted. Thus, the fused image may have an improved contrast of tissues (e.g., soft tissues) in and/or surrounding the target region.

In some embodiments, the processing device 120 may determine information of the target region in the fused image. For example, the information of the target region may include a contour of the target region in the fused image, a contour of a tissue in and/or surrounding the target region in the fused image, etc. The processing device 120 may adjust the treatment plan of the target region of the object based on the information of the target region. In some embodiments, the processing device 120 may identify a change (e.g., a position thereof, a contour thereof) of the target region based on the information of the target region in the fused image, compared to the planned information (e.g., a planned position thereof, a planned contour thereof) of the target region determined based on, e.g., a plan image of the object. In some embodiments, the plan image may be used to determine the treatment plan of the object. In response to determining that the change exceeds a threshold, the processing device 120 may adjust the treatment plan based on the information of the target region in the fused image or the change. In some embodiments, in response to determining that the change exceeds a second threshold larger than the threshold, the processing device 120 may determine a new treatment plan based on the fused image.

It should be noted the above descriptions are for illustration purposes and be non-limiting. In some embodiments, the pre-treatment image may be used as the plan image and used to determine the treatment plan of the object. In some embodiments, the pre-treatment image may be used to adjust the treatment plan regarding the target region determined based on the plan image of the object. For illustration purposes, the processing device 120 may generate a registration result by registering the pre-treatment image and the plan image and adjust the treatment plan based on the registration result. Merely by way of example, if the registration result indicates that a change (e.g., a position thereof, a contour thereof) of the target region with respect to planned information (e.g., a planned position thereof, a planned contour thereof) of the target region exceeds a threshold, the processing device 120 may adjust at least one parameter (e.g., a radiation dose, a radiation duration, a radiation dose distribution) of the target region in the treatment plan. As another example, the processing device 120 may supplement the treatment plan with at least one new parameter of a newly grown target region (e.g., a region different from (and not in) the target region, e.g., a newly grown tumor) determined based on the registration result.

In some embodiments, if the registration result indicates that the change of the target region with respect to planned information of the target region exceeds the threshold, the processing device 132 may generate a notification relating to the registration result. In some embodiments, the processing device 132 may cause the notification to be transmitted to a user (e.g., a doctor) of the radiation system and the user may provide an instruction on how to proceed further in response to the notification. In some embodiments, the processing device 132 may automatically determine how to proceed further based on the registration result.

In some embodiments, the processing device 120 may cause a treatment head of the radiation system to deliver a treatment beam toward the target region of the object in a treatment session based on the treatment plan (or an adjusted treatment plan of the object) and the position information of the target region (e.g., information of the target region in the fused image). The processing device 120 may generate a plurality of images (e.g., 2D images) of the object by causing the plurality of imaging sources of the radiation system to deliver a plurality of treatment imaging beams toward the object during the treatment session. The imaging beams may be delivered concurrently or alternately with the treatment beam. As used herein, an imaging beam delivered during a treatment session is referred to as a treatment imaging beam. A treatment imaging beam may be delivered concurrently or alternately with a treatment beam during a treatment session. As used herein, an imaging performed by an imaging source delivering an imaging beam during a treatment session is referred to as a treatment imaging. A treatment imaging may be performed to monitor the execution of the treatment plan by monitoring the position of the target region and/or tracking the delivery of the treatment beam.

In some embodiments, the position of the target region may change with time due to various motions of organs of the object, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, filling/emptying of bladder, rectum and digestive system, or the like, or any combination thereof. In some embodiments, the whole object may be moved along a direction (e.g., a gantry n axis of the radiation device of the treatment system). At least one of the plurality of images may be used to monitor at least one of the position and/or the motion (or movement) of the target region during the radiotherapy, a change thereof, or a rate of change thereof.

In some embodiments, the processing device 120 may determine the position of the target region based on motion information of at least one organ represented in the at least one of the plurality of images. Taking a specific organ as an example, the processing device 132 may determine motion information of the organ based on organ information of the organ represented in the at least one image. For example, the organ information may include location information of the organ, contour information of the organ, etc. In some embodiments, the processing device 132 may determine the motion information of the organ based on motion information of another organ relating to a motion of the organ In some embodiments, at least one implant may be inserted in the vicinity of the organ and represented in at least one of the at least one image. The processing device 132 may determine the motion information of the organ based on motion information (e.g., location information, contour information) of the at least one implant.

Accordingly, the processing device 120 may adjust a delivery of the treatment beam or adjusting the position information (e.g., the position thereof) of the target region based on the at least one of the plurality of images of the object. In some embodiments, the processing device 120 may determine, based on the at least one of the plurality of images, whether any change or adjustment is needed with respect to the radiotherapy. In some embodiments, when a movement or change of the target region is detected, the processing device 120 may adjust a delivery of the treatment beam or a position of the object based on the at least one of the plurality of images of the object. For example, the processing device 120 may adjust the delivery of the treatment beam or the position of the object by adjusting at least one machine parameter of the radiation device of the radiation system. In some embodiments, the processing device 120 may adjust the position of the target region with respect to the treatment beam to allow the treatment beam to target the target region. In some embodiments, the processing device 120 may adjust a direction of the treatment beam to allow the treatment beam to target the target region. In some embodiments, the processing device 120 may adjust the treatment plan (e.g., a radiation dose of the target region, a radiation duration of the target region) and deliver an adjusted treatment beam to the object from the treatment head and based on the adjusted treatment plan. In some embodiments, the processing device 120 may cause the treatment head to pause the delivery of the treatment beam. For example, the processing device 120 may pause the delivery of the treatment beam, and then adjust the treatment head to aim at the position of the moved or changed target region. As another example, the processing device 120 may pause the delivery of the treatment beam, and then adjust the position of the target region with respect to the treatment beam to make the treatment beam target at the target region. After the delivery of the treatment beam or the position of the object is adjusted, the treatment head may resume the delivery of the treatment beam. In some embodiments, when the movement or change of the target region is detected, the treatment head may terminate the treatment beam delivery. In some embodiments, the processing device 120 may generate a notification based on the detected movement or change of the target region. In some embodiments, the notification may include information of the movement or change of the target region. The notification may be in a form of text, video, audio, or the like, or a combination thereof.

According to the systems and methods described in the present disclosure, during a radiotherapy of a target region, the processing device 120 may automatically generate and/or analyze images to record the radiotherapy, monitor the position of the target region, assess the change of the position of the target region, and/or determine how to proceed further with the radiotherapy (e.g., to continue the radiotherapy as planned, to continue the radiotherapy with a revised plan, or to terminate the radiotherapy, etc.). In some embodiments, the monitoring, assessment, and/or adjustment may be performed semi-automatically with the input of a user (e.g., a doctor). For instance, the processing device 120 may transmit the images to be presented on the terminal 140 (e.g., a display) so that the user may analyze the images and provide an instruction as to how to proceed further with the radiotherapy (e.g., to continue the radiotherapy as planned, to continue the radiotherapy with a revised plan, or to terminate the radiotherapy, etc.). As another example, the processing device 120 may first analyze the images and determine if any change occurs with respect to the target region and how much the change is. The processing device 120 may determine accordingly if any adjustment in the radiotherapy is needed. If the change of the target region or the adjustment needed in the radiotherapy is within a threshold, the processing device 120 may perform the adjustment automatically. In some embodiments, a notification may be generated when the processing device 120 makes such a determination. If the change of the target region or the adjustment needed in the radiotherapy exceeds a threshold, the processing device 120 may generate a notification to, e.g., the user to seek instructions from the user as to how to proceed further.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
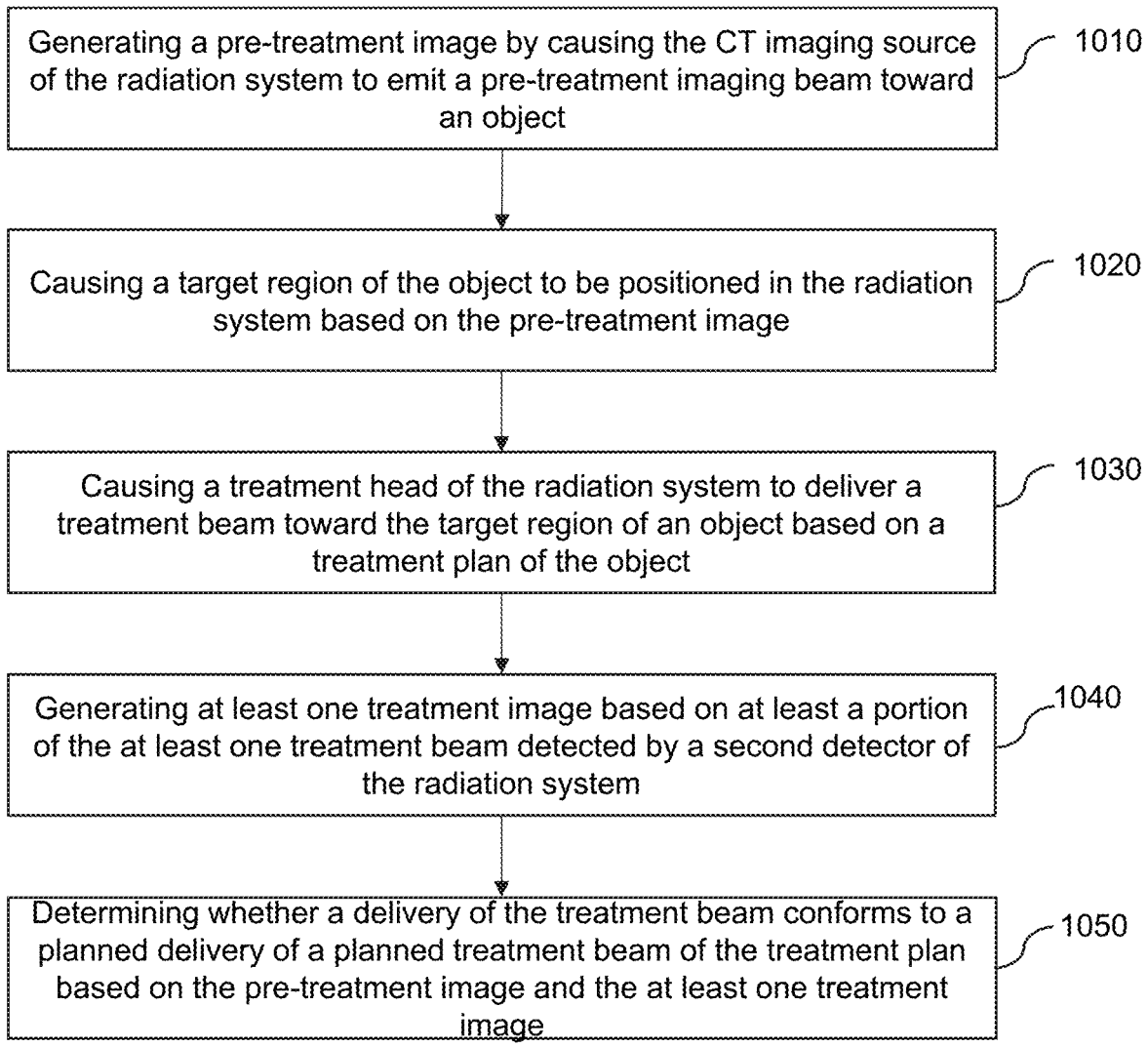
FIG. 10 is a flowchart illustrating an exemplary imaging process of a radiation system according to some embodiments of the present disclosure.

FIG. 10 is a flowchart illustrating an exemplary imaging process of a radiation system according to some embodiments of the present disclosure. The process 1000 may be implemented in the radiation system 100 illustrated in FIG. 1. For example, the process 1000 may be stored in the storage device 130 and/or the storage 620 in the form of instructions (e.g., an application), and invoked and/or executed by the processing device 120 (e.g., the processor 610 illustrated in FIG. 6, or one or more modules in the processing device 120 illustrated in FIG. 8). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In some embodiments, the radiation system may include a plurality of imaging sources and a first detector (e.g., the imaging beam detector illustrated in FIGS. 1-5, e.g., a curvilinear detector). At least two of the plurality of imaging sources may share the first detector. The first detector may be configured to detect at least two imaging beams emitted by the at least two different imaging sources. The detected at least two imaging beams may be emitted by different imaging sources of the at least two imaging sources. The radiation system may be similar to the radiation system 100 illustrated in FIGS. 1-5, the descriptions of which are not repeated here.

In 1010, the processing device 120 (e.g., the image generation module 810, e.g., the first image generation unit 812) may generate a pre-treatment image (e.g., a 3D image) by causing the CT imaging source of the radiation system to emit a pre-treatment imaging beam toward an object. Operation 1010 may be similar to operation 910, the descriptions of which are not repeated here.

In 1020, the processing device 120 (e.g., the position control module 830) may cause a target region of the object to be positioned in the radiation system based on the pre-treatment image. Operation 1020 may be similar to operations 920 and 930, the descriptions of which are not repeated here.

In 1030, the processing device 120 (e.g., the beam control module 840, the first beam control unit 842) may cause a treatment head of the radiation system to deliver a treatment beam toward the target region of the object based on a treatment plan of the object. The treatment beam may be delivered toward the target region of the object to perform a radiotherapy on the target region.

In 1040, the processing device 120 (e.g., the image generation module 810, the second image generation unit 814) may generate at least one treatment image based on at least a portion of the at least one treatment beam detected by a second detector (e.g., the treatment beam detector illustrated in FIGS. 1-5) of the radiation system. In some embodiments, the processing device 120 may obtain an imaging dataset based on at least a portion of each of the at least one treatment beam detected by the second detector and further generate a treatment image (e.g., 2D image) based on the imaging dataset.

In 1050, the processing device 120 (e.g., the monitoring module 850) may determine, based on the pre-treatment image and the at least one treatment image, whether a delivery of the treatment beam (also referred to as a treatment beam delivery) conforms to a planned treatment beam delivery according to the treatment plan. In some embodiments, the at least one treatment image may include one treatment image. The processing device 120 may determine a reference treatment image based on the pre-treatment image and the treatment plan or the adjusted treatment plan of the object. For example, the treatment image and the reference treatment image may be both two-dimensional and from a same view of the object. In some embodiments, the processing device 120 may estimate a reference radiation dose distribution (e.g., a 2D radiation dose distribution) of the treatment beam in the object based on the reference treatment image and an actual radiation dose distribution (e.g., a radiation dose 2D distribution) of the treatment beam in the object based on the treatment image. Further, the processing device 120 may generate a comparison result by comparing the reference radiation dose distribution and the actual radiation dose distribution. The processing device 120 may determine whether the delivery of the treatment beam conforms to the planned treatment beam of the treatment plan based on the comparison result. In response to determining that the comparison result includes that a difference between the reference radiation dose distribution and the actual radiation dose distribution exceeds a threshold, the processing device 120 may determine that the delivery of the treatment beam fails to conform to the planned treatment beam delivery of the treatment plan. In some embodiments, the processing device 120 may further adjust a delivery of the treatment beam or position information (e.g., a position thereof) of the target region according to the process illustrated in FIG. 9.

In some embodiments, the at least one treatment image may include a plurality of treatment images from at least two different views of the object. The processing device 120 may estimate a radiation dose distribution (also referred to as an actual distribution, e.g., a 3D radiation dose distribution) of the treatment beam in the object based on the pre-treatment image and the plurality of treatment images. The processing device 120 may generate a comparison result by comparing the actual radiation dose distribution of the treatment beam and a planned radiation dose distribution in the object. The processing device 120 may determine whether the delivery of the treatment beam conforms to the planned treatment beam of the treatment plan based on the comparison result. For example, in response to determining that the comparison result includes that a difference between the actual radiation dose distribution and the planned radiation dose distribution exceeds a threshold, the processing device 120 may determine that the delivery of the treatment beam fails to conform to the planned treatment beam of the treatment plan. In some embodiments, the processing device 120 may further adjust a delivery of the treatment beam or position information (e.g., a position thereof) of the target region according to the process illustrated in FIG. 9.

In some embodiments, if the comparison result includes that the difference between the reference radiation dose distribution and the actual radiation dose distribution exceeds the threshold, the processing device 132 may generate a notification relating to the comparison result. In some embodiments, the processing device 132 may cause the notification to be transmitted to a user of the radiation system and the user may provide an instruction on how to proceed further in response to the notification. In some embodiments, the processing device 132 may automatically determine how to proceed further based on the comparison result.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 11:
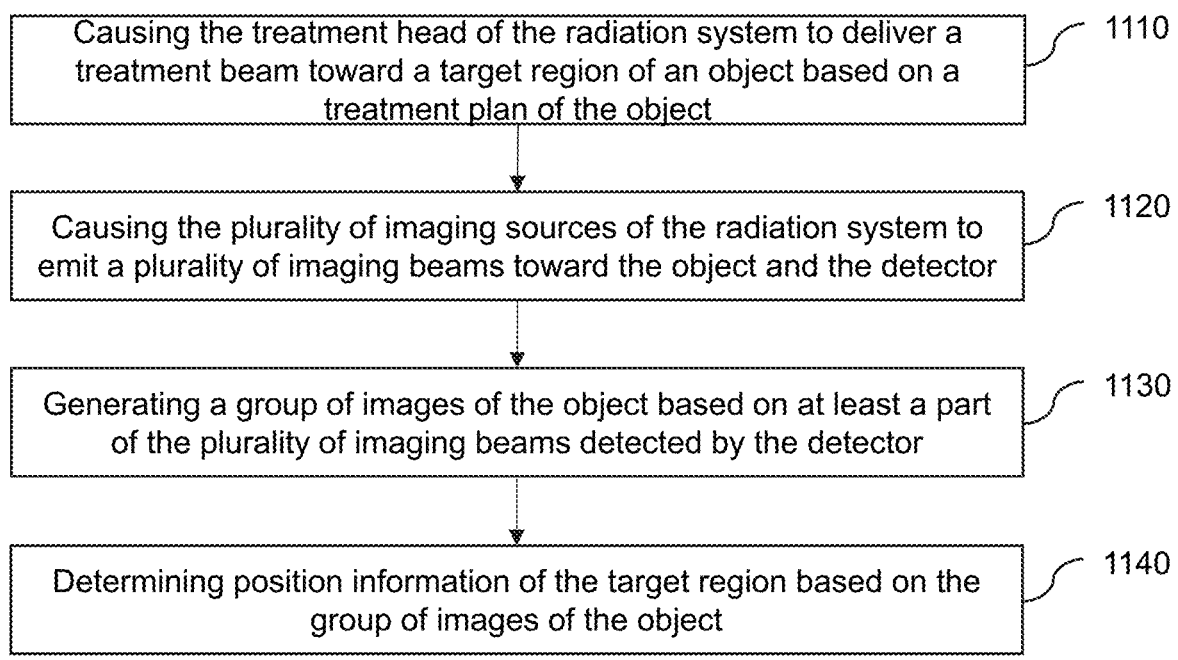
FIG. 11 is a flowchart illustrating an exemplary imaging process of a radiation system according to some embodiments of the present disclosure.

FIG. 11 is a flowchart illustrating an exemplary imaging process of a radiation system according to some embodiments of the present disclosure. The process 1100 may be implemented in the radiation system 100 illustrated in FIG. 1. For example, the process 1100 may be stored in the storage device 130 and/or the storage 620 in the form of instructions (e.g., an application), and invoked and/or executed by the processing device 120 (e.g., the processor 610 illustrated in FIG. 6, or one or more modules in the processing device 120 illustrated in FIG. 8). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In some embodiments, the radiation system may include a plurality of imaging sources, a detector (e.g., the imaging beam detector illustrated in FIGS. 1-5) (e.g., a curvilinear detector), and a treatment head. At least two of the plurality of imaging sources may share the detector. The detector may be configured to detect at least two imaging beams emitted by the at least two different imaging sources. The detected at least two imaging beams may be emitted by different imaging sources of the at least two imaging sources. In some embodiments, at least one of the plurality of imaging sources may rotate with the treatment head. In some embodiments, at least one of the plurality of imaging beams and a treatment beam of the treatment head may be emitted concurrently. The radiation system may be similar to the radiation system 100 illustrated in FIGS. 1-5, the descriptions of which are not repeated here.

In 1110, the processing device 120 (e.g., the beam control module 840, e.g., the first beam control unit 842) may cause the treatment head of the radiation system to deliver a treatment beam toward a target region of an object based on a treatment plan of the object. The treatment beam may be delivered toward the target region of the object to perform a radiotherapy on the target region.

In 1120, the processing device 120 (e.g., the image generation module 810, e.g., the first image generation unit 812) may cause the plurality of imaging sources of the radiation system to emit a plurality of imaging beams toward the object and the detector. The plurality of imaging beams may include a CT imaging beam emitted by the CT imaging source. In some embodiments, the CT imaging beam may be of a fan angle achieved by adjusting an aperture of a collimator of the CT imaging source. In some embodiments, the CT imaging source may be stationary while the CT imaging beam is emitted. A radiation range of the CT imaging source may be of the fan angle. An imaging dataset corresponding to the CT imaging beam of the fan angle can be used to generate a 2D image. In some embodiments, the CT imaging source may rotate or oscillate (rotating by an angle in opposite directions back and forth in an imaging scan) by a rotation angle with respect to a treatment head of the radiation system while the CT imaging beam is emitted. The radiation range of the CT imaging source may be a sum of the fan angle and the rotation angle. An imaging dataset corresponding to the CT imaging beam of the radiation range (e.g., the sum of the fan angle and the rotation angle) can be used to generate a 2D image.

In some embodiments, each of the plurality of imaging beams may impinge on a detection region of the detector. The plurality of detection regions may be at least partially separated from each other. In some embodiments, the detector may detect signals resulting from the imaging beams impinging on the detector. The detector may determine the imaging sources by which the impinging imaging beams are emitted. More descriptions regarding the imaging source determination may be found elsewhere in the present disclosure. See, e.g., FIG. 4 and the description thereof.

In some embodiments, a radiation device of the radiation system may have the configuration 400 in 910 and 920. As described in connection with FIG. 4, the radiation device may include the treatment head, two DR imaging sources, the CT imaging source and the imaging beam detector. The pre-treatment imaging beam may have a relatively small fan angle, in which an imaging beam is delivered by the CT imaging source when the two DR imaging sources are emitting imaging beams.

In 1130, the processing device 120 (e.g., the image generation module 810, e.g., the first image generation unit 812) may generate a group of images of the object based on at least a part of the plurality of imaging beams detected by the detector. In some embodiments, the processing device 120 may generate an imaging dataset based on at least a portion of each of the plurality of imaging beams detected by the detector and further generate an image (e.g., 2D image) based on the imaging dataset. The processing device 120 may generate the group of images based on a plurality of imaging datasets corresponding to the plurality of imaging beams. In some embodiments, at least two of the plurality of images may be from different views of the object and be two-dimensional. For instance, the different views of the object may include a sagittal view, a coronal view, a transverse view, or the like, or any combination thereof, of the object.

In 1140, the processing device 120 (e.g., the position determination module 820) may determine position information (e.g., a position thereof) of the target region based on the group of images of the object. As described in connection with FIG. 9, the position of the target region may change with time due to various motions of organs of the object. In some embodiments, the processing device 120 may determine the position information of the target region based on motion information of at least one organ represented in the groups of images. Taking a specific organ as an example, the processing device 132 may determine motion information of the organ based on organ information of the organ in the groups of images. For example, the organ information may include location information of the organ, contour information of the organ, etc. In some embodiments, the processing device 132 may determine the motion information of the organ based on motion information of another organ relating to a motion of the organ. In some embodiments, at least one implant may be inserted in the vicinity of the organ and represented in at least one of the groups of images. The processing device 132 may determine the motion information of the organ based on motion information (e.g., location information, contour information) of the at least one implant.

In some embodiments, the processing device 120 may generate a second group of images of the object by causing the plurality of imaging sources to deliver a second plurality of imaging beams toward the object and the detector. The second plurality of imaging beams may include a second CT imaging beam of the fan angle emitted by the CT imaging source. The processing device 120 may determine second position information (e.g., a position) of the target region based on the second group of images of the object. The process for generating the second group of images and determining the second position information may be similar to the process for generating the group of images and determining the position information of the target region illustrated above, the descriptions of which are not repeated here. In some embodiments, the group of images of the object may correspond to a first time point, and the second group of images of the object may correspond to a second time point that is different from the first time point.

In some embodiments, the processing device 120 may determine whether to adjust a delivery of the treatment beam and/or the position of the target region based on the position information and/or the second position information. In some embodiments, if a difference between the position information (or the second position information) of the target region determined in 1140 and initial position information of the target region exceeds a threshold, the processing device 120 may adjust the delivery of the treatment beam and/or the position of the target region based on the difference. As used herein, the initial position information of the target region may refer to position information of the target region at the beginning of delivery of the treatment beam in a same treatment session. More descriptions of adjusting the delivery of the treatment beam or the position of the target region may be found elsewhere in the present disclosure, for example, FIG. 9 and the descriptions thereof.

In some embodiments, if the difference between the position information (or the second position information) of the target region determined in 1140 and initial position information of the target region exceeds the threshold, the processing device 132 may generate a notification relating to the difference. In some embodiments, the processing device 132 may cause the notification to be transmitted to a user of the radiation system and the user may provide an instruction on how to proceed further in response to the notification. In some embodiments, the processing device 132 may automatically determine how to proceed further based on the difference.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 132 may obtain a first image based on a first imaging dataset acquired by oscillating one of the plurality of imaging sources (e.g., the CT imaging source) by a first rotation angle with respect to the treatment head of the radiation system within a first time period while a first imaging beam is emitted by the imaging source (also referred to as a tomosynthesis imaging). The processing device 132 may obtain a second image based on a second imaging dataset acquired by oscillating the imaging source by a second rotation angle with respect to the treatment head of the radiation system within a second time period while a second imaging beam is emitted by the imaging source. The first image and the second image may be used to track the position information of the object.

FIG. 12 is a flowchart illustrating an exemplary imaging process of a radiation system according to some embodiments of the present disclosure. The process 1200 may be implemented in the radiation system 100 illustrated in FIG. 1. For example, the process 1200 may be stored in the storage device 130 and/or the storage 620 in the form of instructions (e.g., an application), and invoked and/or executed by the processing device 120 (e.g., the processor 610 illustrated in FIG. 6, or one or more modules in the processing device 120 illustrated in FIG. 8). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In some embodiments, the radiation system may include a plurality of imaging sources and a detector (e.g., the imaging beam detector illustrated in FIGS. 1-5, e.g., a curvilinear detector). At least two of the plurality of imaging sources may share the detector. The detector may be configured to detect at least two imaging beams emitted by the at least two imaging sources. The detected at least two imaging beams may be emitted by different imaging sources of the at least two imaging sources. The radiation system may be similar to the radiation system 100 illustrated in FIGS. 1-5, the descriptions of which are not repeated.

In 1210, the processing device 120 (e.g., the beam control module 840, the first beam control unit 842) may cause the plurality of imaging sources of the radiation system to emit a plurality of imaging beams of different energy levels toward an object and the detector. The plurality of imaging beams may include a CT imaging beam emitted by the CT imaging source, and the CT imaging beam is of a fan angle achieved by adjusting an aperture of a collimator of the CT imaging source. In some embodiments, the CT imaging source may be stationary while the CT imaging beam is emitted. A radiation range of the CT imaging source may be the fan angle. In some embodiments, the CT imaging source may rotate or oscillate (rotating by an angle in opposite directions back and forth in an imaging scan) by a rotation angle with respect to a treatment head of the radiation system while the CT imaging beam is emitted. The radiation range of the CT imaging source may be a sum of the fan angle and the rotation angle. An imaging dataset corresponding to the CT imaging beam of the radiation range (e.g., the sum of the fan angle and the rotation angle) can be used to generate a 2D image.

In some embodiments, each of the plurality of imaging beams may impinge on a detection region of the detector. The plurality of detection regions may be at least partially separated from each other. In some embodiments, the detector may detect signals resulting from the imaging beams impinging on the detector. The detector may determine the imaging sources by which the impinging imaging beams are emitted. More descriptions regarding the imaging source determination may be found elsewhere in the present disclosure. See, e.g., FIG. 4 and the description thereof.

In 1220, the processing device 120 (e.g., the image generation module 810, the first image generation unit 812) may generate an image (e.g., a multi-energy image) of the object based on at least a part of the plurality of imaging beams of different energy levels detected by the detector. In some embodiments, the processing device 120 may generate a primary image of the object based on an imaging dataset corresponding to each of the plurality of imaging beams detected by the detector. The processing device 120 may generate the image by fusing at least two of the plurality of primary images.

In some embodiments, the processing device 120 may cause the CT imaging source to emit a second CT imaging beam of a second fan angle achieved by adjusting the aperture of the collimator of the CT imaging source. The second fan angle may be larger than the fan angle described in 1210. For example, an imaging dataset corresponding to the second CT imaging beam of the second fan angle can be used to reconstruct a 3D image, and an imaging dataset corresponding to the CT imaging beam of the fan angle can be used to generate a 2D image. In some embodiments, the second CT imaging beam may be emitted before a radiotherapy of the target region of the subject or during the radiotherapy of the target region of the subject.

Further, the processing device 120 (e.g., the second image generation unit 814) may generate a second image based on at least a part of the second CT imaging beam detected by the detector. The processing device 120 may generate a fused image by fusing the image and the second image. Compared to the image or the second image, the fused image may have an improved contrast of tissues (e.g., soft tissues) in and/or surrounding the target region. The processing device 120 may determine information of the target region in the fused image. For example, the information of the target region may include a contour of the target region, a contour of a tissue in and/or surrounding the target region, etc. In some embodiments, the processing device 120 may adjust a treatment plan regarding the target region of the object based on the information of the target region in the fused image. More descriptions of adjusting the treatment plan may be found elsewhere in the present disclosure, for example, FIG. 9 and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation system comprising:
a gantry;
a treatment head configured to deliver a treatment beam toward an object;
a detector; and
a plurality of imaging sources configured to deliver a plurality of imaging beams toward the object;
wherein the treatment head, the detector, and the plurality of imaging sources are mounted on the gantry;
at least two of the plurality of imaging sources share the detector; and
the detector is configured to detect at least two of the plurality of imaging beams, the detected at least two imaging beams being emitted by different imaging sources of the at least two imaging sources, wherein the detector includes an anti-scatter grid, the anti-scatter grid including a plurality of portions, an orientation of each of the plurality of portions being adjustable to correspond to a direction of at least one imaging beam emitted by at least one DR imaging source included in the plurality of imaging sources.

2. The radiation system of claim 1, wherein the treatment head, the detector, and the plurality of imaging sources are located in a same plane.

3. The radiation system of claim 1, wherein the plurality of imaging sources include two DR imaging sources, an angle between axes of two imaging beams emitted by the two DR imaging sources being smaller than or equal to 90 degrees.

4. The radiation system of claim 1, wherein the plurality of imaging sources include a computed tomography (CT) imaging source, and an angle between an axis of an imaging beam emitted by the CT imaging source and an axis of a treatment beam emitted by the treatment head is 90 degrees.

5. The radiation system of claim 1, wherein the plurality of imaging sources include a computed tomography (CT) imaging source, and an axis of an imaging beam emitted by the CT imaging source is perpendicular to the detector at a center of the detector.

6. The radiation system of claim 1, wherein the plurality of imaging sources include a computed tomography (CT) imaging source and at least two DR imaging sources, the CT imaging source being located between two of the at least two DR imaging sources.

7. The radiation system of claim 1, wherein a width of the detector exceeds a threshold.

8. A system, comprising:
at least one storage device including a set of instructions;
at least one processor in communication with the at least one storage device and a radiation system, wherein the radiation system includes a detector and a plurality of imaging sources one of which is a CT imaging source, at least two of the plurality of imaging sources share the detector, the detector is configured to detect at least two imaging beams emitted by the at least two imaging sources, the detected at least two imaging beams are emitted by different imaging sources of the at least two imaging sources, and when executing the set of instructions, the at least one processor is configured to cause the system to perform operations including:
generating a pre-treatment image by causing the CT imaging source of the radiation system to emit a pre-treatment imaging beam toward an object;
determining position information of a target region of the object in the radiation system based on the pre-treatment image;
causing the target region of the object to be positioned in the radiation system according to the position information;
causing a treatment head of the radiation system to deliver a treatment beam toward the target region of the object based on a treatment plan of the object and the position information of the target region;
generating a plurality of images of the object by causing the plurality of imaging sources of the radiation system to deliver a plurality of treatment imaging beams toward the object; and
adjusting a delivery of the treatment beam or adjusting the position information of the target region based on the plurality of images of the object, wherein one of the plurality of treatment imaging beams that is emitted by the CT imaging source is adjustably collimated by a collimator of the radiation system, a first fan angle of one of the plurality of treatment imaging beams that is emitted by the CT imaging source is smaller than or equal to a second fan angle of the pre-treatment imaging beam.

9. The system of claim 8, wherein the at least one processor is configured to cause the system to perform the operations including:
generating a second pre-treatment image by causing at least one of the plurality of imaging sources to emit at least one second pre-treatment imaging beam toward the object, wherein the second pre-treatment image is a multi-energy image; and
adjusting a treatment plan of the target region of the object based on the pre-treatment image and the second pre-treatment image.

10. The system of claim 9, wherein the adjusting a treatment plan of the target region of the object based on the pre-treatment image and the second pre-treatment image includes:
generating a fused image by fusing the pre-treatment image and the second pre-treatment image;
determine information of the target region in the fused image; and
adjusting the treatment plan of the target region of the object based on the information of the target region.

11. The system of claim 9, wherein the at least one second pre-treatment imaging beam includes at least two second pre-treatment imaging beams that are of different energy levels and emitted by at least two of the plurality of imaging sources or the at least one of the plurality of imaging sources includes one of the plurality of imaging sources that is configured to emit imaging beams of different energy levels.

12. The system of claim 8, the image comprising at least one organ of the object, wherein the adjusting a delivery of the treatment beam or adjusting the position information of the target region includes:
determining motion information of the at least one organ based on the image; and
adjusting the delivery of the treatment beam or adjusting the position information of the target region based on the motion information of the at least one organ.

13. A system, comprising:
at least one storage device including a set of instructions;
at least one processor in communication with the at least one storage device and a radiation system, wherein the radiation system includes a first detector and a plurality of imaging sources one of which is a CT imaging source, at least two of the plurality of imaging sources share the first detector, the first detector is configured to detect at least two imaging beams emitted by the at least two imaging sources, and the detected at least two imaging beams are emitted by different imaging sources of the at least two imaging sources, and when executing the set of instructions, the at least one processor is configured to cause the system to perform operations including:
generating a pre-treatment image by causing the CT imaging source of the radiation system to emit a pre-treatment imaging beam toward an object;
causing a target region of the object to be positioned in the radiation system based on the pre-treatment image;
causing a treatment head of the radiation system to deliver, based on a treatment plan of the object, at least one treatment beam toward the target region of the object;
generating at least one treatment image based on at least a portion of the at least one treatment beam detected by a second detector of the radiation system; and
determining, based on the pre-treatment image and the at least one treatment image, whether a delivery of the treatment beam conforms to a planned treatment beam delivery according to the treatment plan.

14. The system of claim 13, the at least one treatment image comprising one treatment image, wherein the determining, based on the pre-treatment image and the at least one treatment image, whether a delivery of the treatment beam conforms to a planned treatment beam delivery according to the treatment plan includes:
determining a reference treatment image based on the pre-treatment image and the treatment plan of the object;
generating a comparison result by comparing the reference treatment image and the treatment image; and
determining whether the delivery of the treatment beam conforms to the planned treatment beam delivery of the treatment plan based on the comparison result.

15. The system of claim 14, wherein the treatment image and the reference treatment image are both two-dimensional and from a same view of the object.

16. The system of claim 13, the at least one treatment image comprising a plurality of treatment images from at least two different views of the object, wherein the determining, based on the pre-treatment image and the at least one treatment image, whether a delivery of the treatment beam conforms to a planned treatment beam delivery according to the treatment plan includes:
estimating a radiation dose distribution of the treatment beam in the object based on the pre-treatment image and the plurality of treatment images;
generating a comparison result by comparing the radiation dose distribution of the treatment beam and a planned radiation dose distribution in the object; and
determining whether the delivery of the treatment beam conforms to the planned treatment beam delivery of the treatment plan based on the comparison result.

17. The radiation system of claim 1, wherein the at least two of the at least two imaging sources having different types include a first imaging source of a first type and a second imaging source of a second type that is different from the first type, the first imaging source of the first type being a CT imaging source, and the second imaging source of the second type being a DR imaging source.

* * * * *